(12) United States Patent
Southern et al.

(10) Patent No.: US 7,741,044 B2
(45) Date of Patent: Jun. 22, 2010

(54) LIBRARIES OF OLIGOMERS LABELED WITH DIFFERENT TAGS

(75) Inventors: Edwin Mellor Southern, Oxfordshire (GB); Mikhail Sergeevich Shchepinov, Oxfordshire (GB); John Nicholas Housby, Oxfordshire (GB); Alan Lewis Hamilton, Buckinghamshire (GB); John Kenneth Elder, Oxfordshire (GB)

(73) Assignee: Oxford Gene Technology IP Limited

( * ) Notice: Subject to any disclaimer, the term of this patent is extended or adjusted under 35 U.S.C. 154(b) by 182 days.

(21) Appl. No.: 11/800,241

(22) Filed: May 4, 2007

(65) Prior Publication Data
US 2009/0029866 A1    Jan. 29, 2009

Related U.S. Application Data

(62) Division of application No. 10/843,873, filed on May 11, 2004, now Pat. No. 7,399,846, which is a division of application No. 09/700,462, filed as application No. PCT/GB99/01561 on May 17, 1999, now Pat. No. 6,780,981.

(30) Foreign Application Priority Data
May 15, 1998    (EP)    ................................. 98303873

(51) Int. Cl.
*C12Q 1/68*    (2006.01)
*C12P 19/34*    (2006.01)
*C07H 21/00*    (2006.01)
*C07H 21/02*    (2006.01)

(52) U.S. Cl. .......................... 435/6; 435/91.1; 536/23.1; 536/24.3; 536/24.33; 536/25.3; 536/26.6

(58) Field of Classification Search ................. 536/23.1, 536/24.3, 24.33, 25.3, 26.6; 435/6, 91.1
See application file for complete search history.

(56) References Cited

U.S. PATENT DOCUMENTS

| | | | |
|---|---|---|---|
| 5,622,824 A | 4/1997 | Koster | |
| 6,074,823 A | 6/2000 | Koster | |
| 6,197,498 B1 | 3/2001 | Koster | |
| 6,699,668 B1 * | 3/2004 | Schmidt et al. ................. | 435/6 |

FOREIGN PATENT DOCUMENTS

EP    424819 B1    12/1994

(Continued)

*Primary Examiner*—Jezia Riley
(74) *Attorney, Agent, or Firm*—Lahive & Cockfield, LLP; Megan E. Williams

(57) ABSTRACT

A method of making a set of labelled compounds by the use of a preferably particulate support, comprises dividing the support into lots, performing a different chemical reaction on each lot of the support, e.g. to couple a chemical moiety to that lot of the support, tagging a fraction of each lot of the support with a different label, and combining the said lots of the support. The steps are repeated several times, preferably to build up oligomer molecules carrying labels which identify the nature and position of a monomer unit of the oligomer, and which are releasable from the support. Preferred labels, which are releasable from the compounds by cleavage to provide charged groups for analysis by mass spectrometry, are groups of the trityl (trimethylphenyl) family. Also claimed are libraries of these labels and their use in assays and nucleic acid analysis methods.

10 Claims, 9 Drawing Sheets

FOREIGN PATENT DOCUMENTS

| | | | |
|---|---|---|---|
| WO | 93/06121 | A1 | 4/1993 |
| WO | WO 93/06121 | A1 | 4/1993 |
| WO | 94/21822 | A1 | 9/1994 |
| WO | WO 94/21822 | A1 | 9/1994 |
| WO | 95/04160 | A1 | 2/1995 |
| WO | WO 95/04160 | A1 | 2/1995 |
| WO | 95/28640 | A1 | 10/1995 |
| WO | WO 95/28640 | A1 | 10/1995 |
| WO | 96/30337 | A1 | 10/1996 |
| WO | WO 96/30337 | A1 | 10/1996 |
| WO | 97/27331 | A2 | 7/1997 |
| WO | WO 97/27331 | A2 | 7/1997 |
| WO | 98/20019 | A1 | 5/1998 |
| WO | 98/20020 | A2 | 5/1998 |
| WO | WO 98/20019 | A1 | 5/1998 |
| WO | WO 98/20020 | A2 | 5/1998 |
| WO | 98/31830 | A1 | 7/1998 |
| WO | WO 98/31830 | A1 | 7/1998 |

* cited by examiner

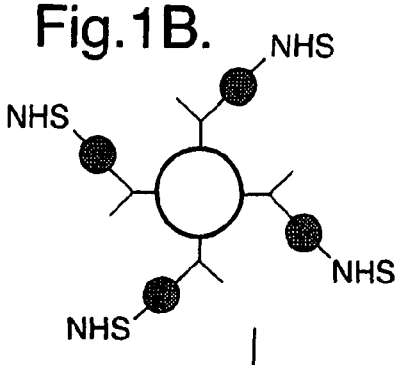
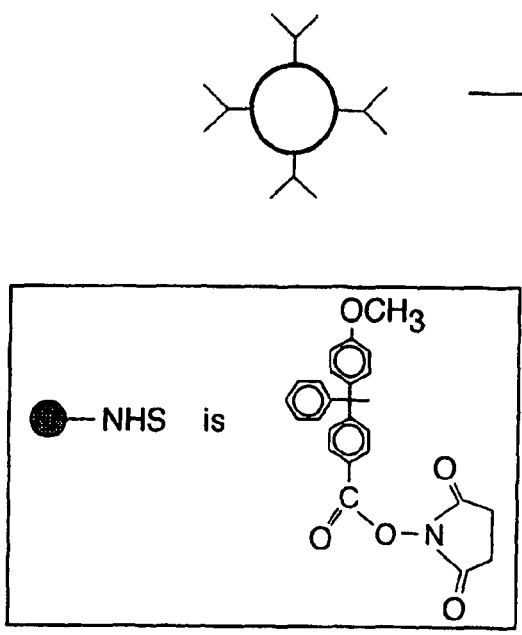
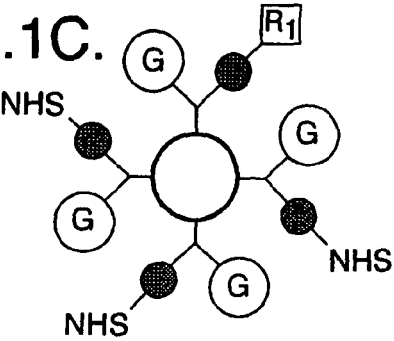
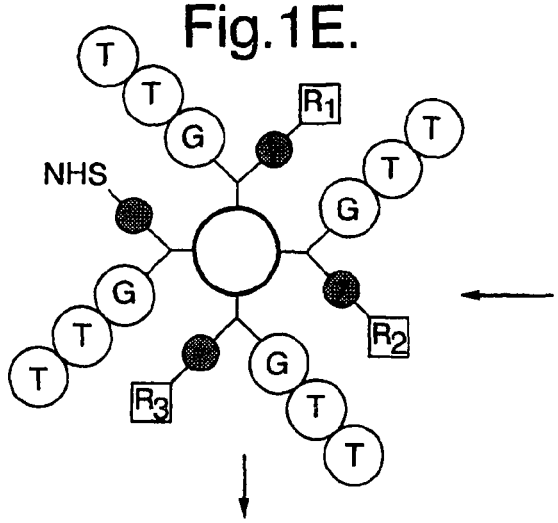
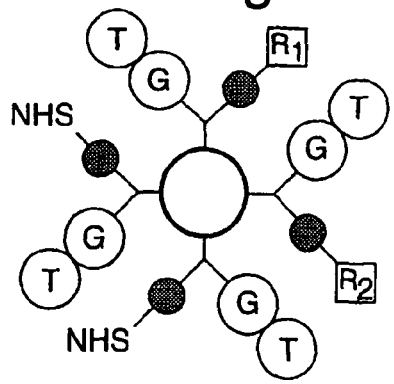
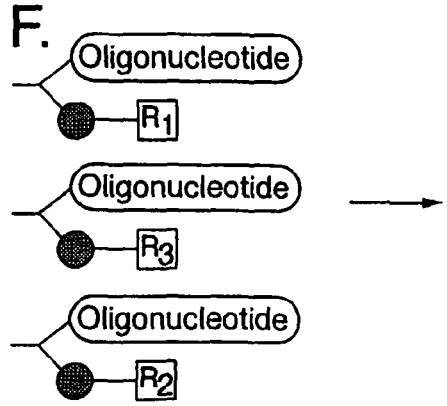
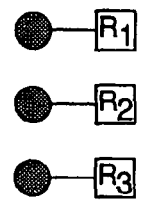

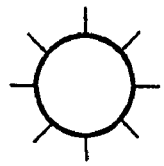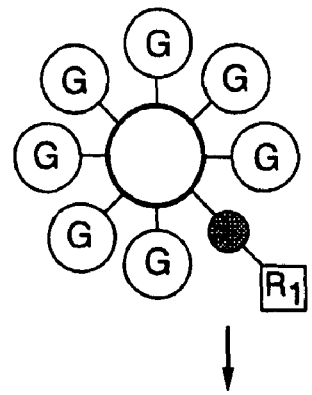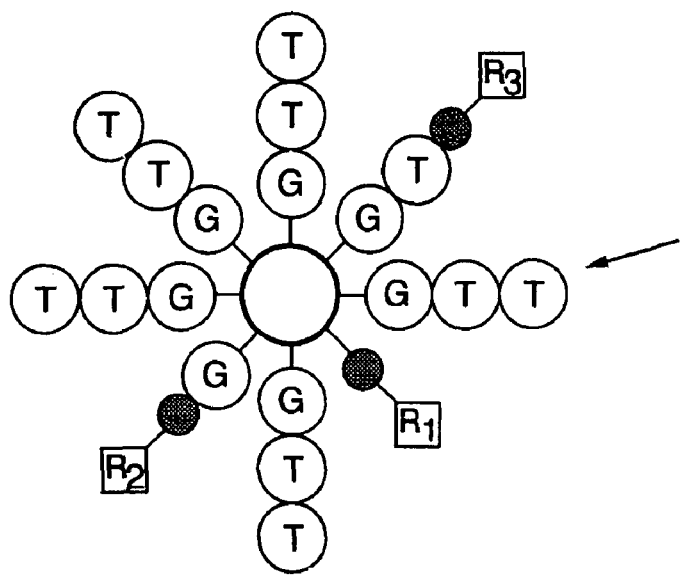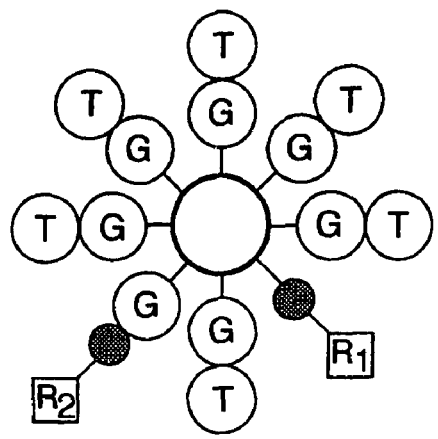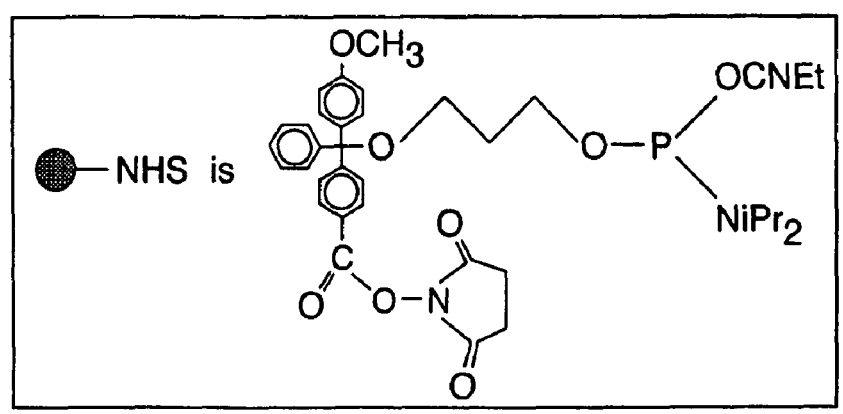

HYBRIDISATION AND LIGATION

Tth DNA ligase

TOF analysis

Figure 9

Hybridisation kinetics of 15-mer to attached oligo

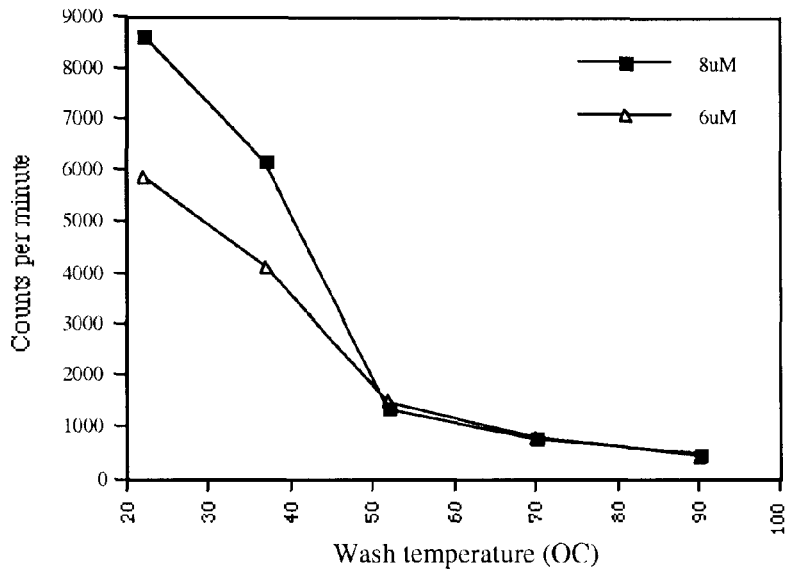

Chart 1. Effect of increased stringency washes on annealing of the 15mer probe oligo to attached template (conditions 1xTth ligation buffer; 0.1%SDS)

Figure 10

Hybridisation of radiolabeled 15-mer to 5'-attached oligo

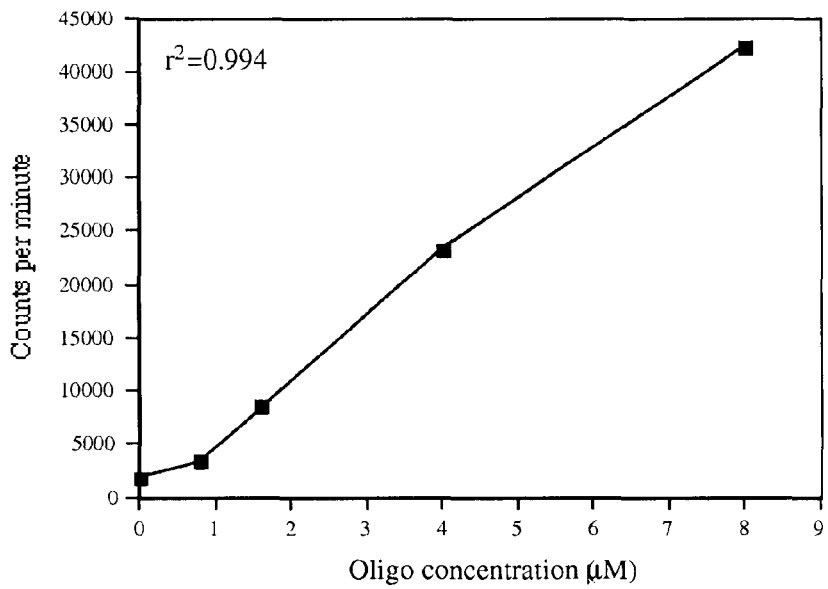

Chart 2. Increase in hybridisation signal of labelled probe is proportional to attached template concentration. (sample washes in 1xTth ligase buffer; 0.1%SDS at 22°C)

LIBRARIES OF OLIGOMERS LABELED WITH DIFFERENT TAGS

RELATED APPLICATIONS

This application is a divisional application of U.S. application Ser. No. 10/843,873, filed May 11, 2004, now U.S. Pat. No. 7,399,846, issued Jul. 15, 2008; which is a divisional application of Ser. No. 09/700,462 filed May 8, 2001, now U.S. Pat. No. 6,780,981, issued Aug. 24, 2004; which is a §371 of PCT Application No. PCT/GB99/01561, filed May 17, 1999; which claims priority to British Application No. 98303873.8, filed May 15, 1998. The entire contents of the aforementioned applications are hereby incorporated herein.

BACKGROUND

This invention concerns reagents of the kind which comprise a product which is built up using stepwise reactions, often chemical reactions, and associated tag moieties which track the synthetic pathway and/or the reagents used. The product will often be an oligomer and the tags define the identity and position of at least one monomer residue in the oligomer. Such reagents are useful in assay methods in which they can generate much more information than can be generated by a simple labelled analyte. Sets and libraries of such reagents can be created by combinatorial chemistry and are valuable for screening large numbers of compound e.g. for biological activity. In preferred systems according to the invention, positively charged tag groups are generated for analysis by mass spectrometry by cleavage, e.g. photocleavage of neutral molecules.

WO 95/04160 describes a reagent which comprises:

a) an analyte moiety comprising at least two analyte residues, and linked to b) a tag moiety comprising one or more reporter groups adapted for detection by mass spectrometry, wherein a reporter group designates an analyte residue, and the reporter group at each position of the tag moiety is chosen to designate an analyte residue at a defined position of the analyte moiety. A plurality of such reagents, each comprising a different analyte moiety, provides a library of reagents which may be used in assay methods involving a target substance. Analysis of the tag moieties indicates the nature of the analyte moiety bound to the target substance.

WO 94/08051 describes a system used to make simultaneously a library of all oligomers each attached to a bead. Any individual bead made by a split and mix process carries a unique chemical product, and this is true of each bead which goes through the same synthetic pathway. Two coupling steps are used at each point in the process: one step affects the synthon or ligand; the other alters the structure of a tag which is also carried on the bead. Tags are designed to identify the steps through which the bead has been taken.

It is an object of this invention to provide a set or library of labelled compounds which may be synthesised on a support and may be used either attached to or separated from that support.

In one aspect the invention provides a method of making a set of labelled compounds, by the use of a support and a set of labels, which method comprises the steps:

a) at least one first or intermediate step comprising dividing the support into lots, performing a different chemical reaction on each lot of the support so as either to modify that lot of the support or to couple a chemical moiety to that lot of the support, tagging a fraction of each lot of the support with a different label, and combining the said lots of the support, and b) at least one intermediate or final step comprising dividing the support into lots, performing a different chemical reaction on each lot of the support, so as either to modify that lot of the support or to couple a chemical moiety to that lot of the support, tagging a fraction of each lot of the support with a different label, whereby each different label is linked to a chemical moiety coupled to the support in a different step and forms with that chemical moiety a labelled compound which is separable from the support, and combining the said lots of the support.

The method uses a support which is repeatedly divided into lots which are then recombined. The support may be a massive support e.g. a flat sheet or silicon chip or microtitre plate which is divided e.g. by masking into regions for performing the different chemical reactions. The support may be a polymeric material which is soluble in some solvents and not in others, and which is separated into lots or recombined e.g. by precipitation or dissolution. Most usually the support will be particulate, e.g. pins or fibres or capillaries or preferably beads. Derivatised beads for performing combinatorial chemistry by a split and mix strategy are commercially available and can be used here. A preferred particulate support comprises beads having cleavable linkers, wherein each cleavable linker has one group for defined chemical procedures e.g. oligomer synthesis and another group for labelling. By this means it is possible at the end of the synthesis, to recover the labelled chemical products e.g. oligomers into solution.

The method of the invention involves performing at least one step a) and at least one step b), most usually at least three steps in all. Each step involves performing a reaction, generally but not necessarily a chemical reaction. An example of such a reaction might be the removal of a protective group so as to leave a primary amine or hydroxyl or carboxylic acid group. Most usually, the chemical reaction involves coupling a chemical moiety to the support. The chemical moiety will usually be an organic chemical group, for example as described in WO 94/08051. While successive chemical moieties may be attached to the support through separate linkers, more usually, successive chemical moieties will be joined to each other to form a chain extending from the support. Preferably the chemical moieties are monomer units which are built up to form oligomer chains.

In a preferred method according to the invention, the set of labelled compounds is a library of $n^s$ labelled oligomers, where n is the number of different monomer units and s is the number of monomer units in each labelled oligomer, wherein step a) is performed once to couple a different monomer unit to each lot of the support, and step b) is performed s−1 times.

The oligomer may be for example an oligonucleotide or an oligopeptide. When the oligomer is an oligonucleotide or analogue, then n is generally 4. When the oligomer is an oligopeptide, then n is generally about 20 when only natural amino acids are used. But the principles of the invention are equally applicable to other oligomers formed from other polymerisable monomers. The value of s is not critical, and may typically be from 2-100 e.g. 3-20 or more.

The fraction of each lot that is tagged in each step is generally less than 50%. Preferably from 0.25% to 25% of each lot of the support is tagged in each step with a different label. Preferably the support has cleavable linkers, wherein each cleavable linker has at least one group for chemical reaction e.g. chemical synthesis and another group for labelling. Preferably each resulting labelled compound comprises a single label and at least one chemical moiety.

The method involves the use of a set of up to and including n×s different labels. Although the nature of the labels is not critical, it is a preferred feature of the invention that each different label be distinguishable by the analytical procedure used to detect the labels. Groups used as labels should be much more stable to acidic (or other chemical) treatment involved in oligomer synthesis compared to the protecting groups commonly used (e.g. DMT groups to provide 5' or 3'-protection in nucleotide synthons). Preferred labels are those in which a charged group, preferably a positively charged group is generated by cleavage e.g. photocleavage of a neutral molecule for analysis by mass spectrometry. Examples of such preferred labels are discussed below.

In a preferred embodiment, a split and mix strategy requires a solid support carrying cleavable linkers with three arms—one to attach to the solid support through a cleavable bond; one to initiate synthesis of a chemical product e.g. oligomer; and a third for attachment of the tags. The sites for coupling of synthon and tag monomers will optionally be protected by removable groups. The process can be illustrated by the synthesis of oligomers on a particulate solid support.

At each stage in the synthetic route, the particles of the support are first combined and mixed, and then divided into n lots, where n is the number of different monomers—4 in the case of natural nucleotides—and each monomer is coupled to its site on one lot of the support. A unique tag representing the monomer just added and its position in the sequence is then coupled to a fraction of the support, corresponding approximately to the number of monomers in the final oligomer (i.e. 1/s for an oligomer with s monomer units). Alternatively, a tag may be coupled to a fraction of the support before or simultaneous with, rather than after, the monomer which it represents. Partial coupling may be achieved in a number of different ways. For example, (i) a protecting group on the site may be partially removed; (ii) the coupling may be taken to a fraction of completion; (iii) a fraction of the support may be removed and coupling taken to completion before the fraction is returned to the pool. As the coupling steps proceed, the oligomer is extended one unit at a time, and the tags are added one at a time. The end result is a mixture of molecules on each particle; each molecule will carry the same sequence of monomers in the oligomer, but a fraction, 1/s for s-mers, will carry the tag added at any of the s coupling steps.

An example of this embodiment is shown in FIG. 1 of the accompanying drawings. At A, is illustrated a solid support in the form of a bead derivatised with cleavable linkers each having two arms. At B, one of the two arms of each linker has been reacted with a trityl group carrying a succinimidyl substituent. At C, the other branch of each linker has been reacted with a nucleotide residue shown as G; and one portion of the NHS groups has been substituted by a label $R_1$. At D, oligonucleotide synthesis has continued by formation of dimer chains GT; and a second portion of the NHS groups has been substituted by a second label $R_2$. At E, oligonucleotide synthesis has continued by formation of chains GTT; and a third portion of the NHS groups has been substituted by a label $R_3$. At F, ammonolysis of the beads has given rise to a pool of oligonucleotides of the same sequence, in which each one is attached to a different tag. At G, photolysis has detached three derivatised trityl groups for analysis by mass spectrometry. The split and mix approach ensures that all the oligonucleotides attached to any bead have the same s-mer sequence; and that the bead also carries a total of s different labels, each of which indicates the position and identity of one monomer residue of the oligomer.

An alternative way of partial coupling is to cap the extension of a fraction of the chemical compounds e.g. oligomers with a stable tag group at each extension step. For example, in the case of oligonucleotide synthesis, the coupling agents could include a small proportion of a phosphoramidite protected by one of the stable trityl groups described below as mass tags. Elongation will produce a major proportion with the desired base and a small fraction with a corresponding tag marking the nature and position of the base.

An example of this embodiment is illustrated in FIG. 2 of the accompanying drawings. Oligonucleotide synthesis is performed on derivatised beads A, the first, second and third stages of this synthesis being shown as B, C and D. Each of four phosphoramidite reagents contains a small fraction depending on the length of the oligomer, preferably less than 1/s, of a capping phosphoramidite bearing a very acid-stable NHS-substituted trityl group. After each stage of synthesis, all incorporated NHS groups are reacted with an amine thereby attaching a label. For synthesis of longer oligonucleotides o-methyl phosphoramidite could be used to withstand repetitive amination reactions. The three different labels used in B, C and D are shown in FIG. 2 as $R_1$, $R_2$ and $R_3$. At the end of synthesis, the oligonucleotides are deprotected by treatment with ammonia, but remain attached to the beads. Thus each bead carries a plurality of s-mer oligomers of identical sequence, together with a total of s different substituted trityl labels each of which indicates the identity and position of a monomer unit of the oligomer. The beads are used in an assay procedure. Thereafter photolysis of a bead generates charged substituted trityl moieties E for detection by mass spectroscopy. Alternatively the labelled oligonucleotides can be released into solution.

In another aspect, this invention provides a set of labelled compounds wherein a molecule of a compound of the set is tagged with a single label which identifies the nature and/or the position of a component of that molecule, and different molecules of the same compound are tagged with different labels. The set of labelled compounds may be releasably attached to a solid support e.g. beads; or may be mixed together in solution.

Also envisaged according to the invention is a library consisting of a plurality of the sets of the labelled compounds as herein defined, e.g. a library of $n^s$ labelled oligomers, where n is the number of different monomer units and s is the number of monomer units in each labelled oligomer.

In another aspect (e.g. as illustrated in FIG. 2) the invention provides a reagent comprising a solid support which carries on its surface molecules of an oligomer, with different oligomer molecules having the same sequence wherein the oligomer molecules include some shorter oligomer molecules and a shorter oligomer molecule carries a label which identifies the nature and position of a monomer unit of the oligomer molecule. A library consists of a plurality of the said reagents, in which the solid supports are preferably beads.

Preferred features of the labels used herein are:

They should be attached by linkages which are stable to the chemical procedures used in the preparative method and those used to detach the resulting chemical compound e.g. oligomer from a solid support. The trityl residues described below are stable throughout the procedures used to synthesise oligonucleotides.

They should have properties which allow up to n×s labels to be distinguished by the analytical procedure used to detect them, as each chemical moiety or reaction is tagged uniquely. In an example below, it is shown how all 262144 nonanucleotides can be coded uniquely using 36 different tag monomers. This number is readily achieved using the trityl derivatives described below. Alternatively, but less preferably, the same number of 9-mers could be coded for by 18 binary tags or even by a unique combination of 9 tags as described in WO 94/08051.

On cleavage, e.g. by photocleavage, chemical cleavage using acidic conditions, or enzymatic methods, from the parent molecule, they should generate stable species, either neutral molecules or preferably charged ions, for analysis by mass spectrometry. Mass spectrometry is a preferred method of analysis, allowing for the simultaneous detection of hundreds of labels. This property, of generating a preferably charged group by photocleavage of a neutral molecule, ensures that the ions are brought into the vapour phase without the need for added matrix. Therefore it is not necessary to search for "hot spots" as is the case when matrix is added. Not having matrix present also allows for further biochemical processes e.g. oligonucleotide ligation. In certain cleavage methods such as those involving acid, the addition of matrix may enhance the sensitivity of detection.

Bearing in mind these criteria, preferred labels according to the invention are groups of the formula $R^1R^2R^3C$— where $R^1$, $R^2$ and $R^3$ are the same or different and each is a monocyclic or fused ring aromatic group that is substituted or unsubstituted. These are groups of the trityl (triphenylmethyl) family. Other possible labels include troponium and those discussed in WO 97/27331. Trityl groups have the desirable property that they are readily cleaved by illumination with a laser in a mass spectrometer. Sensitivity of detection of trityl groups is high because of the stability of the positively charged carbonium ion. This sensitivity gives rise to a number of advantages, e.g. there are enough trityl groups in a molecular monolayer such as results if trityl labelled molecules are tethered covalently to a surface.

Preferably at least one of $R^1$, $R^2$ and $R^3$ carries a substituent selected from $C_1$-$C_{20}$ alkoxy or hydrocarbyl either unsubstituted or substituted by carboxylic acid, sulphonic acid, nitro, cyano, hydroxyl, thiol, primary, secondary or tertiary amino, primary or secondary amido, anhydride, carbonyl halide or active ester. Hydrogen atoms in these substituents may be partly or wholly replaced by deuterium or halogen e.g. fluorine; this improves the range available for analysis by mass spectrometry.

Preferably each of $R^1$, $R^2$ and $R^3$ is aryl, more preferably phenyl. While substituents may be present at any point in the aromatic (e.g. phenyl) ring, para-substituents are convenient and are preferred. The substituents may be present to confer desired physical or chemical properties on the trityl (or other) group. For example, electron withdrawing groups at ortho or para positions increase the stability of trityl groups to acid hydrolysis. Substituents may be present to alter the formula weight of the trityl (or other) group, so as to enable easy detection and discrimination by mass spectrometry. Non-radioactive isotopic substituents are suitable for this purpose, e.g. small alkyl groups containing 1, 2 or 3 deuterium atoms. Preferred substituents are amine or amide groups. There is a considerable number of amines having different molecular weights that are commercially available and that can be used to provide substituted trityl groups having distinctive formula weights, see for example Table 1 below.

The masses of the majority of commercially available amines lie in the range of 50-250 Da. For some applications it would be desirable to have up to a few hundred mass-tags. The resolution of the tags in TOF-mass spectrometry was found to be satisfactory with at least 4 Da difference between the masses of tags. Therefore, the above range of amines can only yield about 50 different tags. To increase this amount using the same pool of amines, it is possible to incorporate two or four or even more amide substituents per trityl group, and this is illustrated in the experimental section below.

The principle of the system is illustrated in FIG. 3 of the accompanying drawings. At A, an oligonucleotide has been synthesised on a CPG support. At B, a 5'-hydroxyl group of the oligonucleotide has been replaced by an NHS-substituted trityl group. At C, an amide group NHR has been introduced, in which R is chosen to have a characteristic formula weight. At D, the labelled oligonucleotide has been released into solution for use in an assay procedure. At E, the NHR-substituted trityl group has been volatilised by photolysis and has been detected by mass spectrometry.

The above mass spectrometry labels are useful in a variety of other biochemical methods and manipulations. Thus according to another aspect, the invention provides a nucleic acid determination method, which method comprises providing a labelled oligonucleotide or nucleic acid, and removing the label by cleavage to give a charged species which is subjected to mass spectrometry. Preferably nucleic acid analysis, e.g. sequencing or sequence difference analysis, is performed by the use of a labelled primer and/or labelled chain extending nucleotides and/or labelled chain terminating nucleotide analogues, wherein the label is as described above.

In another aspect, the invention provides an assay method in which a labelled probe is partitioned into two fractions of which one is determined, the probe comprising a ligand joined to a label by a link which is cleavable to give a charged species for analysis by mass spectrometry. The invention also includes a library of probes, each comprising a ligand joined to a label by a link which is cleavable to give a charged species for analysis by mass spectrometry, wherein each different probe has a different label. Preferably the labels are as described above.

Certain of the labels are envisaged as new compounds per se according to the invention. These are compounds of the formula $R^1R^2R^3CY$; where Y is a leaving group e.g. halide or tosylate for displacement by a nucleophile e.g. a thiol, alcohol or amine group; and $R^1$, $R^2$ and $R^3$ are as defined above, with the proviso that $R^1$, $R^2$ and $R^3$ together carry at least two amide groups and/or at least two reactive groups for coupling e.g. N-hydroxysuccinimide ester groups.

In addition, the inventors have manufactured a disposable glass insert for use as a target surface for laser desorption ionisation mass spectrometry. The glass target may be used for analysis of samples spotted and dried directly on to the glass surface. The glass target may also be chemically activated and used as a solid support for immobilised nucleic acids or other compounds using methods already developed. Complementary nucleic acids, mass-tagged oligonucleotides or other compounds isolated and localised on the glass target may then be subjected to direct analysis by laser desorption ionisation mass spectrometry. One advantage of using a solid support is that it may be introduced directly into a mass spectrometer for subsequent detection and avoids unnecessary liquid handling of the sample. Organic polymeric surfaces such as polypropylene are possible alternatives to glass.

Any surface chemistry developed for attachment of compounds to glass may be used to immobilise these compounds directly on to a target for laser desorption ionisation mass spectrometry or matrix-assisted laser desorption ionisation mass spectrometry. For example 3-mercaptopropyl silane derivatisation (Rogers, et al 1999) or amine derivatisation (Beattie, et al 1995; Chen, et al 1999) for the attachment of nucleic acids. The glass inserts are significantly cheaper than conventional inserts and are truly disposable. Mass spectrometry performance is unaffected. (See Example 4 below).

The invention also provides an insert for use as a target for laser desorption ionisation mass spectrometry, which insert has a target surface of glass carrying an immobilised compound for analysis.

The invention also provides a kit comprising a mass spectrometer and a supply of inserts, for use as targets for laser desorption mass spectrometry, having target surfaces of glass.

In a preferred embodiment of the invention, a system for analysing nucleic acids comprises:

a solid support carrying an array of nucleic acids to act as targets for analysis or as probes to capture a target;

oligonucleotide reagents tagged with moieties suitable for analysis by mass spectrometry;

reagents and apparatus for biochemical procedures to allow specific interaction between the tagged oligonucleotides and the target;

a means to introduce the samples into a mass spectrometer;

a mass spectrometer.

In a more preferred embodiment of the invention, a system for analysing nucleic acids on a solid support comprises:

a solid support carrying an array of nucleic acids to act as targets for analysis or as probes to capture a target;

oligonucleotide reagents, tagged with moieties suitable for analysis by mass spectrometry;

reagents and apparatus for biochemical procedures to allow specific interaction between the tagged oligonucleotides and the target carried out on the solid support surface;

a means to introduce the solid support into a mass spectrometer;

a mass spectrometer.

In a further preferred embodiment of the invention, an automated system for analysing nucleic acids comprises:

oligonucleotide reagents, tagged with moieties suitable for analysis by mass spectrometry;

a mass spectrometer;

a computer to carry out the analysis;

software to interpret a mass spectrum.

Computer programs are provided for oligonucleotide sequence determination by mass spectrometry.

Each base and base position in an oligonucleotide is associated with a unique mass tag.

For oligonucleotides of length s, 4s tags are needed to distinguish between all $4^s$ possible oligonucleotides.

Careful choice of tags ensures that all tags have sufficiently different masses to avoid ambiguity in tag assignment when analysing a mass spectrum.

The chemical formula for each tag is known, so each tag's monoisotopic mass can be calculated.

The isotopic abundances of the elements in the tag are also known, so a complete distribution of masses and abundances of all isotopic variants of each tag can be calculated.

For the tags used so far, the major heavy isotopes of a tag are those due to the presence of $^{13}C$, and a typical isotopic abundance distribution is that for $C_{27}H_{30}O_2N$, with relative abundances of 73:22:3 for isotopic masses 400.228, 401.231 and 402.234 respectively. These abundance distributions characterise the tags' presence in a mass spectrum, and help to distinguish tags from other features in the spectrum.

The use of elements such as chlorine or bromine in mass tags further aids tag detection and identification, since these elements have markedly different isotopic abundances from that of carbon:

for $^{35}Cl:^{37}Cl$ the abundance ratio is 76:24 and for $^{79}Br:^{81}Br$ it is 51:49.

Mass tags containing these elements will therefore have their own characteristic isotopic distributions. In general, the aim is to design tags with characteristic sets of masses which facilitate identification amongst a background of chemical 'noise'.

Mass standards are included in each spectrum to allow the spectrum's mass axis to be calibrated. Use of mass standards both within and on either side of the tag mass range ensures accurate mass measurement throughout this range. Ions representing a complete set of possible masses are often seen in mass spectra and these represent the ideal calibration set.

A program has been written to calculate the isotopic abundance distribution and corresponding isotopic masses of any mass tag, using the known masses and isotopic abundances of the elements in each tag. This information is calculated for all mass tags available for use in tagging oligonucleotides.

A second program uses this information to determine the presence of mass tags and hence the sequence in the mass spectrum generated by an oligonucleotide, and works as follows. For each base position in the oligonucleotide, the four regions of the mass spectrum corresponding to the masses of the four possible tags (including their isotopic variants) are examined and compared with the expected tag spectrum. The comparison is done either by identification of spectral peak positions and amplitudes and their differences from those of the potential tag, or by measuring the sum of squares of residuals between the experimental spectrum and that expected from the potential tag. In either case, the four potential tags are ranked by the chosen measure and the best tag is used to assign a base to that base position.

A more powerful approach is to examine each possible oligonucleotide in turn, obtaining a goodness of fit over all s tag regions by the method described above, and then ranking the oligonucleotide sequences by this measure.

Reference is directed to the accompanying drawings in which:—

FIG. 1 is a diagram of a coding strategy using trityl-based mass-tags which are attached to oligonucleotides in solution.

FIG. 2 is a diagram of a coding strategy using trityl-based mass tags, with mass tags and oligonucleotides attached to beads.

FIG. 9 is a graph demonstrating the effect of increased stringency washes on annealing of a 15mer probe oligo to an attached template (conditions 1×Tth ligation buffer; 0.1% SDS).

FIG. 10 is a graph demonstrating that an increase in hybridisation signal of labelled probe is proportional to the attached template concentration. (sample washes in 1×Tth ligase buffer; 0.1% SDS at 22° C.).

EXPERIMENTAL

Figure 3:
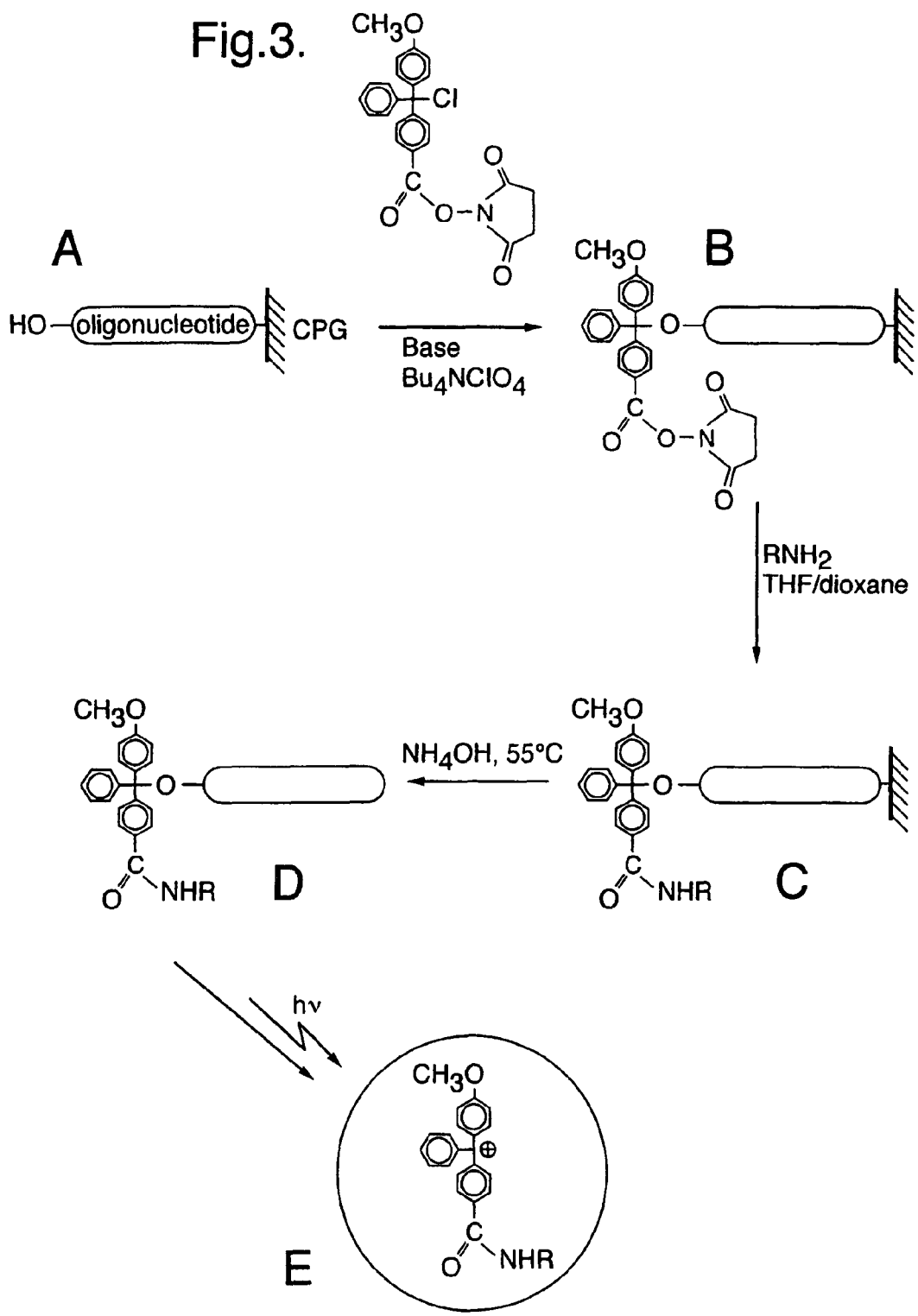
FIG. 3 is a diagram showing the synthesis and detection of an MMT-tagged oligonucleotide.
Figure 4:
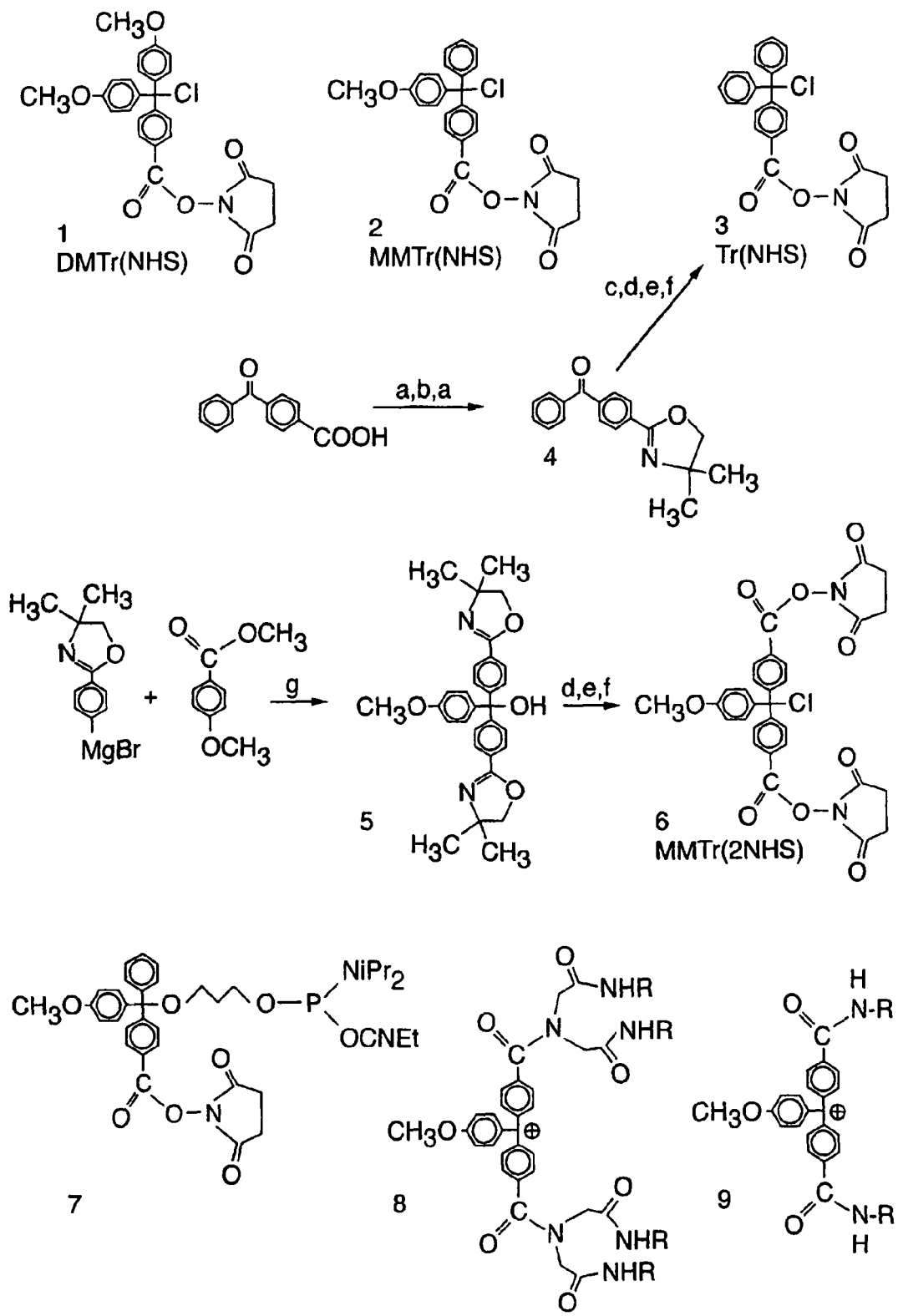
FIG. 4 shows synthesis of various trityl-based mass-tags.

A series of compounds has been made with different substituents at the phenyl rings of the core trityl structure. Some of these compounds are believed to be new and form additional aspects of this invention. The chemistry involved is illustrated in FIG. 4 of the accompanying drawings. The compounds and their properties are as follows.

FIG. 4.

a. $SOCl_2$, reflux. b. 2-amino-2-methylpropanol-1, 2.5 eqv. c. phenylmagnesium bromide. d. 80% AcOH, 48 h. e. NHS, DCC. f. AcCl, toluene, reflux. g. Grignard synthesis. 3 is alternatively synthesised from benzophenone and 4-bromophenyl oxazoline.

Example 1

N-succinimidyl-4-[bis-(4-methoxyphenyl)-chloromethyl]-benzoate (1) was synthesised according to the reported procedures (1,2).

N-succinimidyl-4-[(4-methoxydiphenyl)-chloromethyl]-benzoate (2) was synthesised according to the reported procedures (1,2), but 4-methoxybenzophenone was used in the Grignard synthesis instead of 4,4'-dimethoxybenzophenone. $^1$H-NMR (CDCl$_3$, δ, md): 7.95-6.8 (m, 13H, arom.), 3.8 (s, 3H, OCH$_3$), 2.88 (s, 4H, NHS). Mass-spectrum, TOF (no matrix): (MI+H$^+$).

N-succinimidy-4-[bis-(phenyl)-chloromethyl]-benzoate (3) was synthesised according to the reported procedures (1,2), but benzophenone was used in the Grignard synthesis instead of 4,4'-dimethoxybenzophenone. $^1$H-NMR (CDCl$_3$. δ, md): 8.0-6.8 (m, 14H, arom.), 2.88 (s, 4H, NHS). Mass-spectrum, TOF (no matrix): (MI+H$^+$).

The formation of the Grignard reagent from 2-(4-bromophenyl)-4,4-dimethyl-1,3-oxazoline is rather unreliable and irreproducible, even using RED-Al® (Aldrich) as an activator. To take advantage of commercially available Grignard reagents (Aldrich), the inventors synthesised oxazolyl-protected 4-carboxybenzophenone (4) starting from 4-carboxy benzophenone. Following the Grignard reaction, subsequent steps were similar to those used for compounds 1-3.

2-(4-benzophenyl)-4,4-dimethyl-1,3-oxazoline (4). 4-benzoylbenzoic acid (50 g, mmol) was refluxed in 300 ml of thionyl chloride for 3 h, evaporated (the product crystallises from the oil) and then evaporated with toluene (2×30 ml). The residue was dissolved in 254 ml of dry methylene chloride. To this ice-cooled solution, 46 g (2.5 eqv) of 2-amino-2-methylpropanol-1 in 150 ml of dry methylene chloride was added dropwise for 2 h. The solution was stirred overnight at room temperature, and the precipitate was washed several times with methylene chloride. Combined fractions were evaporated, carefully dissolved in 350 ml of thionyl chloride and refluxed for 4 h. The reaction mixture was evaporated to ⅓, poured into 2 L of dry ether and kept overnight at 4° C. The precipitate of hydrochloride was dissolved in 1 L of water at 10° C., and 300 ml of 5M KOH was added to it with stirring. The mixture was extracted with chloroform (3×350 ml), organic phase dried over CaCl$_2$ and evaporated. The crystalline product was obtained from toluene. 42 g (75%) white crystalline solid, mp 81° C. $^1$H-NMR (CDCl$_3$. δ, md): 8.2-7.2 (m, 9H, arom.), 4.18 (s, 2H, CH$_2$), 1.45 (s, 6H, CH$_3$). Mass-spectrum, MALDI-TOF: 279.091 (MI), 302.085 (MI+Na$^+$), 319.656 (MI+K$^+$).

The masses of the majority of commercially available amines lay in the range of 50-250 Da. For some applications it would be desirable to have up to a few hundred mass-tags. The resolution of the tags in TOF mass-spectrometry was found to be satisfactory with at least 4 Da difference between the masses of tags. Therefore, the above range of amines can only yield about 50 different tags. To increase this amount using the same pool of amines, the inventors synthesised another trityl-based compound with two activated carboxyl groups (6), which upon reaction with amine would form two amide bonds thus giving other series of mass-tags as compared, for example, to (2). Additional increase of mass can be achieved by attaching even more amines to trityl core by using, for example, (8).

4,4'-[bis-(2-(4,4-dimethyl-1,3-oxazolyl))]-4"-methoxytritanol (5). To 1.5 g of magnesium turnings activated with iodine 15.34 g (mmol) of bromophenyl oxazoline in 150 ml of dry THF and a droplet of RED-A1® were added with stirring and the mixture was refluxed for 3 h, cooled to room temperature and 4.64 g (mmol) of methyl 4-methoxybenzoate in 40 ml of dry THF was added dropwise. The mixture was gently refluxed for 6 h, cooled to room temperature and 10 ml of water was added with stirring. Organic phase was carefully decanted and residue washed several times with small portions of THF. Combined organic fractions were evaporated and purified (flash-chromatography) to give 11.4 g (84%) of light yellow solid. Mass-spectrum, MALDI-TOF: 467.545 (MI-OH), 484.869 (MI). $^1$H-NMR (CDCl$_3$, δ, md): 7.95-6.75 (m, 12H, arom.), 4.12 (s, 4H, CH$_2$), 3.78 (s, 3H, OCH$_3$), 1.37 (s, 12H, CH$_3$).

4,4'-[bis-(2-(succinimidylcarboxy)]-4"-methoxytrityl chloride (6). The solution of 5 (10 g, mmol) in 250 ml of 80% acetic acid was kept at 72° C. for 48 h, evaporated and then evaporated with water (2×50 ml). The product was dissolved in 75 ml of 50% EtOH/water, refluxed for 3 h and evaporated to ⅓. The mixture was then dissolved in 100 ml of water and acidified with 3M HCl to pH 1-2. The precipitate was dissolved in chloroform, dried (Na$_2$SO$_4$) and evaporated to dryness and additionally dried in vacuo overnight. Dicarboxylic acid obtained was dissolved in 100 ml of dry THF. 8.5 g (mmol) of N-hydroxysuccinimide was added and the mixture was cooled to 0° C. Dicyclohexylcarbodiimide (8.5 g, mmol) in 20 ml of dry THF was added dropwise with stirring. The reaction mixture was stirred 1 h at 0° C. and overnight at room temperature. Dicyclohexylurea was filtered off and organic phase was evaporated to dryness and purified (flash-chromatography) to give 8.5 g (%) of white yellow-white solid. Mass-spectrum, MALDI-TOF: 554.703 (MI+OH), 570.794 (MI). $^1$H-NMR (CDCl$_3$ δ, md): 8.2-6.75 (m, 12H, arom.), 3.81 (s, 3H, OCH$_3$), 2.9 (s, 8H, CH$_2$). This compound was converted into corresponding trityl chloride by refluxing in AcCl/toluene for 3 h. The reaction mixture was then evaporated to ⅓. ⅔ of volume of toluene was added, the mixture was again evaporated to ⅓ and used without further purification.

To introduce a tagging moiety during oligonucleotide synthesis (FIG. 4), we synthesised non-nucleoside phosphoramidite synthon 7 based on propanediol structure, which provides reactivity similar to the standard A, C, G and T phosphoramidites. The MMTr(NHS)Cl has reduced reactivity compared to both DMTrCl and DMTr(NHS)Cl, and it is important, when synthesising 7, to carry out the tritylation reaction at low temperatures to prevent the formation of ester bond between excess of propanediol and the activated carboxyl group (data not shown). The phosphoramidite 7 was stable in acetonitrile solution at room temperature for at least 2 days.

O$^1$-{[4-(succinimidylcarboxy)]-4'-methoxytrityl}-1,3-propanediol

The title compound was synthesised according to a published procedure (4), but the tritylation step was carried out in pyridine at 0° C. overnight without a catalyst. Monoprotected propanediol was obtained with a yield of 55% after flash-chromatography as a white foam. Mass-spectrum, MALDI-TOF (α-cyano-4-hydroxycinnamic acid): 488.76 (MI). $^1$H-NMR (CDCl$_3$, δ, md): 8.15-6.8 (m, 13H, arom.), 3.8 (s, 3H, OCH$_3$), 3.79 (t, 2H, CH$_2$OH), 3.28 (t, 2H, J=6 Hz, MMTr (NHS)OCH$_2$), 2.9 (s, 4H, succinimide), 1.89 (quin, 2H, CH$_2$CH$_2$CH$_2$).

$O^1$-{[4-(succinimidylcarboxy)]-4'-methoxytrityl}-$O^3$-(N,N-diisopropylamino-2-cyanoethoxy phosphinyl)-1,3-propanediol (7)

Phosphitylation of monoprotected propanediol was carried out as described in (4) to give the title phosphoramidite as a white foam in 70% yield. $^{31}$P-NMR (CDCl$_3$, δ, md): 144.512. Mass-spectrum, MALDI-TOF (dihydroxybenzoic acid): 689.934 (MI).

Analysis of trityl-based tags. 0.1 M solutions of compounds 1, 2, 3 and 6 were prepared in the mixture of THF/dioxane (1:1). 110 μl of these solutions were mixed with 40 μl (80 μl in case of 6) of 0.5-1 M solutions of different amines (Table 1). The mixtures were then analysed with and without matrix either directly or when mixed in different combinations.

To evaluate these modified trityl blocks as precursors for mass-tags, compounds 1 and 2 were used to synthesise 5'-protected thymidine. 0.1 M solutions of these nucleosides and also of compounds 3 and 6 in OH-form (tritanols) in THF were reacted with 0.5-1 M solutions of amines in THF or dioxane (5 eqv. of amine for mono-NHS-based compounds and 10 eqv. for 6), by mixing 200 μl of each of tritylated compounds with the corresponding amount of an amine solution and allowing them to react for 5 min. The reaction mixtures were then analysed by mass spectrometry without matrix, to prevent formation of molecular ions, by applying 1 μl of these mixtures directly onto a sample target plate and allowing them to dry. Typical results are presented in Table 1. For all trityl derivatives, the compounds which gave the strongest signal were selected and analysed as a mixtures by mixing all and applying 1 μl of the mixture to the target plate. Excellent results were achieved, both with and without matrix.

All synthesised trityl blocks were tested for acid-liability by treatment with 2-5% TsOH or HClO$_4$ of corresponding 5'-thymidylates and TLC-analysis of the products after quenching with sat. sodium bicarbonate. As expected, there was about one order of magnitude difference in stability between DMTr, MMTr and Tr. Corresponding NHS-derivatives were about twice as stable, i.e. the stability was: DMTr<DMTr(NHS)<MMTr<MMTr(NHS)<Tr<Tr(NHS).

To be used as a tag in oligonucleotide synthesis, the trityl group should give clean high intensity signal in (MA)LDI-TOF analysis. It should also survive several steps of acidic treatment used to remove 5'-DMTr group in oligonucleotide synthesis, that is, be orthogonal to other protective groups involved. (The NHS-group is stable to the conditions of oligonucleotide synthesis, see Example 2). The MMTr(NHS) group is preferred as the one to meet both these demands. It remained attached to a primary hydroxyl group after at least 5-8 cycles of acidic deprotection in oligonucleotide synthesis using twofold diluted standard solution of trichloroacetic acid in dichloromethane and a reduced deprotection time. For analysis, it was easily released using 3-4% TFA in the same solution (~1-3 min).

REFERENCES

1. Gildea, B. D., Coull, J. M. and Koster, H. (1990) *Tet. Lett.*, 31, 7095-7098.
2. Coull, J. M., Gildea, B. and Koster, H. Pat. U.S. Pat. No. 5,410,068 (1995).
3. Gait, M. J. (1984) *Oligonucleotide Synthesis. A Practical Approach*. IRL Press, Oxford, UK.
4. Seela, F. and Kaiser, K. (1987) Nucl. Acids Res. 15, 3113-3129.

TABLE 1

| | | | Observed Mass of Tritylamide (no matrix) | | | |
|---|---|---|---|---|---|---|
| # | MW, Da | Chemical name | Tr(NHS) (3) | MMTr(NHS) (2) | DMTr(NHS) (1) | MMT, (2NHS) (6) |
| 1. | 17.03 | Ammonia | 286.27 | 316.25 | 346.31 | 359.36 |
| 2. | 31.06 | Methylamine | 300.33 | 330.32 | 360.43 | 387.45 |
| 3. | 45.09 | Ethylamine | 314.38 | 344.35 | 374.45 | 415.54 |
| 4. | 59.11 | Propylamine | 328.39 | 358.44 | 388.53 | 443.64 |
| 5. | 73.14 | Butylamine | 342.47 | 372.46 | 402.51 | 471.71 |
| 6. | 74.09 | Glycinamide (xHCl) | — | 372.44 | 403.60 | 474.55 |
| 7. | 85.15 | Cyclopentylamine | 354.42 | 384.47 | 414.53 | 495.71 |
| 8. | 87.17 | Amylamine | 356.43 | 386.60 | 416.52 | 499.73 |
| 9. | 87.17 | 2-Amino-3-methylbutane | 356.38 | 386.42 | 416.50 | 499.65 |
| 10. | 89.14 | 2-Amino-1-methoxypropane | 358.35 | 388.34 | 418.14 | 503.57 |
| 11. | 89.14 | 4-Amino-1-butanol | 358.40 | 388.39 | 418.41 | 503.65 |
| 12. | 89.14 | 2-Amino-2-methyl-1-propanol | 358.39 | 388.43 | 418.51 | 503.66 |
| 13. | 97.12 | Furfurylamine | 366.43 | 396.42 | 426.54 | 519.64 |
| 14. | 99.18 | Cyclohexylamine | 368.47 | 398.52 | 428.58 | 523.78 |
| 15. | 101.19 | Hexylamine | 370.56 | 400.55 | 430.69 | 527.76 |
| 16. | 103.17 | 5-Amino-1-pentanol | 372.52 | 402.60 | 432.63 | 531.78 |
| 17. | 103.19 | Thiomorpholine | 372.47 | 402.46 | 432.55 | 531.72 |
| 18. | 105.14 | 2-(2-Aminoethoxy)-ethanol | 374.45 | 404.53 | 434.56 | 535.66 |
| 19-. | 113.20 | Cycloheptylamine | 382.50 | 412.49 | 442.58 | 551.86 |
| 20. | 114.19 | 1-(2-Aminoethyl)-pyrrolidine | 383.43 | 413.45 | 443.59 | 553.68 |
| 21. | 115.22 | Heptylamine | 384.49 | 414.48 | 444.55 | 555.81 |
| 22. | 121.18 | Phenethylamine | 390.52 | 420.48 | 450.58 | 567.63 |
| 23. | 122.17 | 2-(2-Aminoethyl)-pyridine | 391.62 | 421.54 | 451.63 | 569.84 |
| 24. | 125.18 | 1-(3-Aminopropyl)-imidazole | 394.24 | 424.58 | 454.73 | 576.34 |
| 25. | 127.23 | Cyclooctylamine | 396.62 | 426.61 | 456.77 | 580.00 |
| 26. | 128.18 | α-Amino-ε-caprolactam | 397.56 | 427.54 | 457.65 | 581.91 |
| 27. | 128.22 | 2-(2-Aminoethyl)-1-methylpyrrolidine | 397.64 | 427.67 | 457.71 | — |
| 28. | 128.22 | 1-(2-Aminoethyl)-piperidine | — | 427.62 | 457.69 | 581.91 |
| 29. | 129.25 | Octylamine | 398.64 | 428.57 | 458.70 | 583.92 |
| 30. | 130.19 | 4-(2-Aminoethyl)-morpholine | 399.56 | 429.49 | 459.60 | 585.94 |
| 31. | 130.23 | N,N-Diethyl]-1,3-propanediamine | 399.53 | 429.55 | 459.66 | 585.85 |
| 32. | 135.17 | 3-Phenylpropylamine | 404.54 | 434.51 | 464.66 | 595.72 |

TABLE 1-continued

| | | | Observed Mass of Tritylamide (no matrix) | | | |
|---|---|---|---|---|---|---|
| # | MW, Da | Chemical name | Tr(NHS) (3) | MMTr(NHS) (2) | DMTr(NHS) (1) | MMT, (2NHS) (6) |
| 33. | 135.21 | 1-(4-Methylphenyl)-ethylamine | 404.59 | 434.55 | 464.65 | 595.89 |
| 34. | 137.18 | 4-Methoxybenzylamine | 406.57 | 436.55 | 466.63 | 599.85 |
| 35. | 137.18 | 2-Phenoxyethylamine | 406.61 | 436.55 | 466.56 | 599.91 |
| 36. | 139.17 | 4-Fluoro-(α-methyl-benzylamine | 408.62 | 438.58 | 468.63 | 663.91 |
| 37. | 142.20 | 1-(3-Aminopropyl)-2-pyrrolidinone | 411.63 | 441.67 | 471.77 | 610.02 |
| 38. | 143.14 | 3,5-Difluorobenzylamine | 412.56 | 442.55 | 472.67 | 611.85 |
| 39. | 143.27 | Nonylamine | 412.67 | 442.65 | 472.74 | 612.10 |
| 40. | 144.22 | 4-(3-Aminopropyl)-morpholine | 413.57 | 443.52 | 473.58 | — |
| 41. | 147.22 | 1,2,3,4-Tetrahydro-1-naphthylamine | 416.55 | 446.49 | 476.59 | 619.82 |
| 42. | 149.06 | 2,2,3,3,3-Pentafluoropropylamine | 418.50 | 448.46 | 478.58 | 623.78 |
| 43. | 149.24 | 1-Methyl-3-phenylpropylamine | 418.65 | 448.61 | 478.58 | 623.95 |
| 44. | 149.24 | 4-Phenylbutylamine | 418.64 | 448.61 | 478.73 | 623.95 |
| 45. | 151.21 | Norephedrin | 420.62 | 450.63 | 480.77 | 627.98 |
| 46. | 151.21 | 2-(4-Methoxyphenyl)-ethylamine | 420.63 | 450.66 | 480.71 | 627.95 |
| 47. | 151.25 | 1-Adamantylamine | 420.69 | 450.62 | 480.75 | 628.06 |
| 48. | 155.29 | 4-tert-Butylcyclohexylamine | 424.73 | 454.68 | 480.75 | 636.06 |
| 49. | 155.29 | Menthylamine | 424.68 | 454.63 | 484.77 | 635.82 |
| 50. | 156.27 | 1-(3-Aminopropyl)-2-pipecoline | — | 455.63 | 485.79 | — |
| 51. | 157.22 | 1-Naphtalenemethylamine | 426.52 | 456.49 | 486.55 | 639.69 |
| 52. | 157.30 | Decylamine | 426.68 | 456.64 | 486.70 | 640.02 |
| 53. | 158.29 | 2-Amino-5-diethylaminopentane | 427.75 | 457.67 | 487.81 | 642.12 |
| 54. | 160.22 | Tryptamine | 428.67 | −459.64 | 489.72 | 645.97 |
| 55. | 162.24 | 1-Phenylpiperazine | 431.69 | 461.70 | 491.75 | 649.99 |
| 56. | 167.21 | 2,6-Dimethoxybenzylamine | 436.63 | 466.60 | 496.65 | 659.94 |
| 57. | 171.33 | Undecylamine | 440.85 | 470.76 | 500.88 | 668.21 |
| 58. | 175.15 | 4-(Trifluoromethyl-benzylamine | 444.65 | 475.66 | 504.52 | 676.03 |
| 59. | 176.26 | 1-Benzyl-3-aminopyrrolidine | 445.72 | 474.53? | 505.74 | 677.93 |
| 60. | 180.23 | 1-(4-Fluorophenyl)piperazine | 449.60 | 477.64 | 509.71 | 685.94 |
| 61. | 181.25 | Dicyclohexylamine | — | — | — | — |
| 62. | 183.25 | Aminodiphenylmethane | 452.60 | 482.57 | 512.63 | 691.80 |
| 63. | 185.36 | Dodecylamine | 454.80 | 484.79 | 514.86 | 696.16 |
| 64. | 190.29 | 4-Amino-1-benzylpiperidine | 459.73 | 489.69 | 519.83 | 706.00 |
| 65. | 191.27 | 2-Benzyloxycyclopentylamine | 460.80 | 490.68 | 520.54 | 708.02 |
| 66. | 193.15 | 3-Fluoro-5-(trifluoromethyl)-benzylamine | 462.75 | 492.60 | 522.64 | 711.88 |
| 67. | 197.28 | 1,2-Diphenylethylamine | 466.75 | 496.68 | 526.83 | 719.96 |
| 68. | 199.38 | Tridecylamine | 468.90 | 498.85 | 528.93 | 724.30 |
| 69. | 200.26 | 4-(2-Aminoethyl)benzenesulfonamide | 469.59 | 499.59 | 529.68 | 725.81 |
| 70. | 206.75 | 1-(2-Ethoxyphenyl)piperazine (XHCl) | 477.71 | 502.68 | 535.99 | — |
| 71. | 207.28 | Amino-2,2-dimethyl-4-phenyl-1,3-dioxane | 476.53 | 506.49 | 536.44 | 752.22 |
| 72. | 213.41 | Tetradecylamine | 482.81 | 512.79 | 542.81 | 752.30 |
| 73. | 221.31 | 9-(Methylaminomethyl)-anthracene | 490.77 | 520.83 | — | — |
| 74. | 227.44 | Pentadecylamine | 496.88 | 526.90 | 557.03 | 780.21 |
| 75. | 231.30 | 1-Pyrenemethylamine | 509.83 | 540.93 | 571.08 | 808.36 |
| 76. | 241.46 | Hexadecylamine | 512.74 | 542.71 | 572.78 | 812.17 |
| 77. | 243.15 | 3,5-Bis(trifluoromethyl)-benzylamine | — | — | — | 860.46 |
| 78. | 269.50 | Octadecylamine | 538.99 | 568.92 | 599.15 | 864.52 |
| 79. | 297.57 | Didecylamine | 566.97 | 596.99 | 627.02 | 920.55 |
| 80. | 339.61 | Hexetidine | 609.00 | 638.99 | — | — |

Example 2

An oligonucleotide trimer, 5'-GAA-3', was synthesised directly on PEG-grafted Rapp beads on 1 μmol scale of synthesis using standard 3'-phosphoramidites. The beads were then subject to 4 more steps of oligonucleotide synthesis, this time according to split-and-mix strategy as outlined in FIG. 2, using 7 and 16 different amines, thus producing a library of 256 different 7-mers. After ammonia deprotection the beads were washed and hybridised to 0.05 μmol of 5'-Cy5-TTC-.CAG.T (10) (SEQ ID NO: 1) and 5'-Cy5-TTC.TAT.T (11) (SEQ ID NO: 2) as described below.

ca 3-6 mol % of 7 was mixed with standard A, C, G and T phosphoramidites prior to oligonucleotide synthesis. Assuming the stepwise yield of oligonucleotide synthesis to be about 99%, for an 8-mer library synthesised using 7 as a 5% additive to all bases, that would give ca 60% of all sites of the beads occupied by full length oligonucleotides. The concentration of the first tag (5% of all initial sites) would be about two-fold greater than that of the last tag (5% of the remaining 60% of the sites), which still makes it possible to detect all of them in the same mixture. Oligonucleotide synthesis was carried out on a 4-column ABI machine. After each oxidation step, the columns were removed and treated with different amines. No particular rationale was used when choosing masses of tags to be used for encoding of particular base/position. But in principle, certain mass-ranges could be used to code for either a base type (i.e. all As are coded by tags ranging from 400 to 500 Da, all Cs—by tags in the interval of 500-600 Da, etc) or, alternatively, the position of the base might be a determining factor (i.e., position #1, or a 3'-end, (A, C, G or T) is coded by mass-tags ranging from 400-420 Da, position #2- by 420-440 Da, etc).

Beads were selected by hybridisation with Cy5-labelled oligonucleotide. The size of Rapp-beads (~0.3 mm) allows for manual removal of positively identified beads, visible with the naked eye, from the pool. For smaller beads, automated methods such as Flow-cytometry (FACS), might be used. Selected beads were detritylated and the mixtures of tags released analysed by mass spectrometry.

To eliminate any problem of gradual loss of encoding MMTr-based tags during the detritylation step in oligonucleotide synthesis, 5'-Fmoc-protective strategy has also been used, thus omitting the use of acidic conditions altogether. After each oxidation step, the columns were removed from the synthesizer, and the beads were treated with corresponding amines washed with acetonitrile and then treated with 0.1 M DBU in acetonitrile to remove Fmoc-protection. The tags encoding for 9-mer oligonucleotide synthesised using this strategy were detected using (MA)LDI-TOF analysis. For longer sequences, the 3'-methylphosphoramidites of 5'-Fmoc-protected nucleosides could be preferably used instead of cyanoethoxy phosphoramidites, to prevent the untimely loss of the CNET-group due to the treatment with amines and DBU.

Oligonucleotide synthesis. Oligonucleotide synthesis was carried out using commercially available standard A, C, G and T, PAC, fluorescein and Cy5 phosphoramidites according to the manufacturer's protocols.

Synthesis of the combinatorial library. Phosphoramidite 7 was added to standard A, C, G and T phosphoramidites up to 3-6 mol. % of total amount of phosphoramidite. 35-40 mg (ca. 2500 beads) of Rapp TentaGel Macrobeads were placed in each of four polypropylene DNA synthesis columns (1 μmol scale, Glen Research, USA). The oligonucleotide synthesis was carried out on 1 μmol scale using phosphoramidite mixtures: A+7, C+7, G+7 and T+7, according to the manufacturer's protocol, but the supply of deblocking reagent (diluted to 50% of its original concentration with methylene chloride) to the columns was reduced to 10-15 sec, with subsequent waiting step (10 sec) and another portion of acid (10 sec). Subsequent thorough acetonitrile washing of the columns ensured that all DMTR+ is desorbed. Before each detritylation step, the columns were washed with acetonitrile using Manual Control mode, and then treated with corresponding amines (0.3-0.5 ml of 0.5-1 M solutions in dioxan/THF, depending on the solubility of an amine) for 1 min using 1 ml syringes. The columns were then washed excessively with acetonitrile and dried in vacuo for 15 min. The beads from all columns were then combined together in a 0.3 ml reaction vial with conical chamber (Pierce), mixed and then split again in four portions by pipetting the suspension of beads in acetonitrile (about 1 volume of solvent per 1 volume of beads) using a 1 ml Eppendorf tip. The procedure was repeated till the end of the synthesis. The beads were then washed, dried, deprotected for 14 h in 1.5 ml of concentrated ammonia at 55° C., then washed several times with distilled water, dried and stored at 4° C.

Hybridisation of the combinatorial library and detritylation. The beads were hybridised to 5'-Cy5-labelled 7-mer oligonucleotides 5'-TTC.CAG.T (10) (SEQ ID NO: 1) and 5'-TTC.TAT.T (11) (SEQ ID NO: 2) in 1.5 ml of 3.5 M TMA buffer (51) in a 4 ml vial which was rotated on a Spiramix 10 machine overnight at 8° C. The beads were then washed 5 times with TMA buffer at the same temperature, transferred onto a surface of a 7.5×5 cm microscope slide and the excess of the buffer removed by blotting with tissue paper. Coloured or otherwise identified beads were then removed using tweezers (usually about 30-50 beads), washed with water, acetone and dried. The trityl tags were cleaved by treating the beads with 0.08-0.1 ml of 3-4% (v/v) solution of trifluoroacetic acid in standard Deblok Solution (Cruachem; trichloroacetic acid in dichloromethane) for 3-4 min. Supernatant was evaporated several times with acetone or methanol to remove the acids and the residue was analysed by (MA)LDI-TOF. Excellent quality results were obtained.

Example 3

Thiolated oligonucleotides have previously been used to immobilise PCR products onto gold monolayers (e.g. Hegner et al.). The attachment is due to bonding between the gold and the thiol group. Using this chemical reaction it is possible to immobilise any gene, or region of any gene, onto the gold plated surface of a mass spectrometer target plate, via a thiol linkage.

This example illustrates the immobilisation of PCR products to the gold surface of mass spectrometer target plates; hybridisation and ligation of pairs of oligonucleotides, one of which defines the locus and the other a putative allele; the allele is characterised by the detection of a trityl tag(s) by mass spectrometer. The example given uses M13 mp18 ssDNA as a putative target region.

Figure 5:
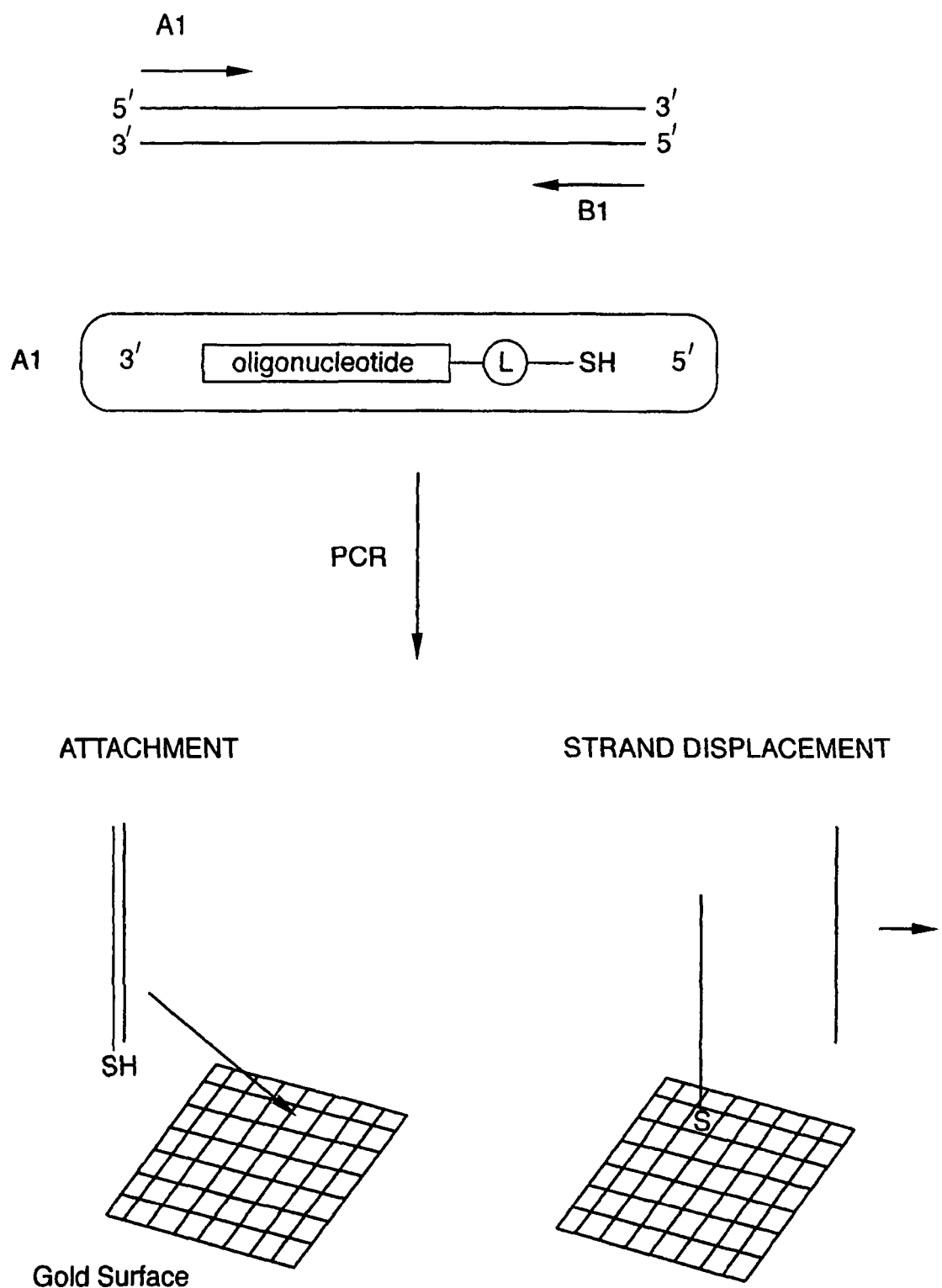
FIGS. 5 and 6 are diagrams showing a PCR and immobilisation strategy followed by hybridisation and ligation.

PCR and Immobilisation (FIG. 5)

A 225 base pair PCR product was amplified from M13 mp18 ssDNA using two oligonucleotide primers; A1 5'ACTGGCCGTCGTTTTAC3'—(SEQ ID NO: 3); B1 5'AAGGGCGATCGGTGCGG 3'—(SEQ ID NO: 4). A1 was synthesised with the addition of a 17 atom linker molecule, and a thiol group, to the 5' end using conventional phosphoramidite chemistry (see figure). The thiol group was activated with a 200 fold excess of DTT, and 5 ng of product was spotted on to the gold target plate. Incubation in 100% humidity overnight was sufficient to immobilise the PCR product. Excess template was removed by flooding the plate with 10 mM Tris-HCl (pH 7.5).

Figure 6:
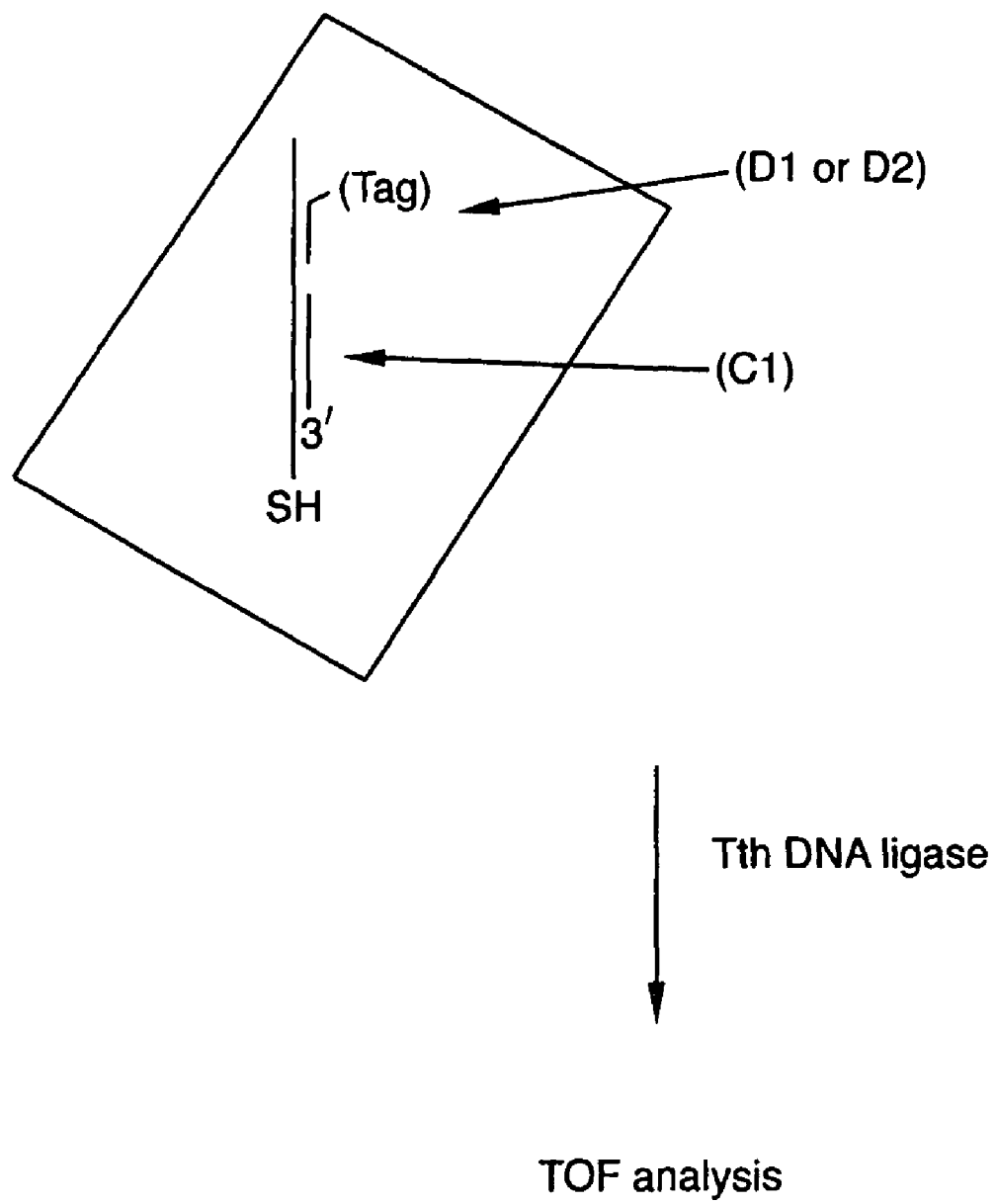

Hybridisation and Ligation (FIG. 6)

The oligonucleotide defining the locus, C1-5'GTAAAAC-GACGGCCAGT3' (SEQ ID NO: 5) was synthesised with a phosphate group coupled to the 5' end. Two putative allele defining oligonucleotides were synthesised, D1 and D2-5'CACGACGTT3' (SEQ ID NO: 6) differing only in their 5' terminus where D1 was tagged with dimethoxytrityl and D2 with monomethoxytrityl. Both oligonucleotides were synthesised using conventional phosphoramidite chemistry and were fully complementary to the PCR amplified product.

Ligation and hybridisation was at 46° C. (Housby and Southern, 1998) overnight in 100% humidity, and under saturating concentrations of oligonucleotides C1 and D1 and/or D2. For ligation, a thermostable DNA ligase, Tth, was used because of its high temperature optimum for ligation and high degree of discrimination for the 3' end of substrate oligonucleotide. Residual unligated oligonucleotides were removed by washing.

Mass Spectrometer Analysis

The mass spectrum of monomethoxytrityl (MMT, mass 272) clearly demonstrated cleavage of MMT from the ligated product. No matrix was used to assist ionisation. Control samples showed no detectable peaks at 272.

The same experiment using dimethoxytrityl as the tagged oligonucleotide demonstrates that DMT also "flies" well and has a peak at 303 mass units.

Figure 7:
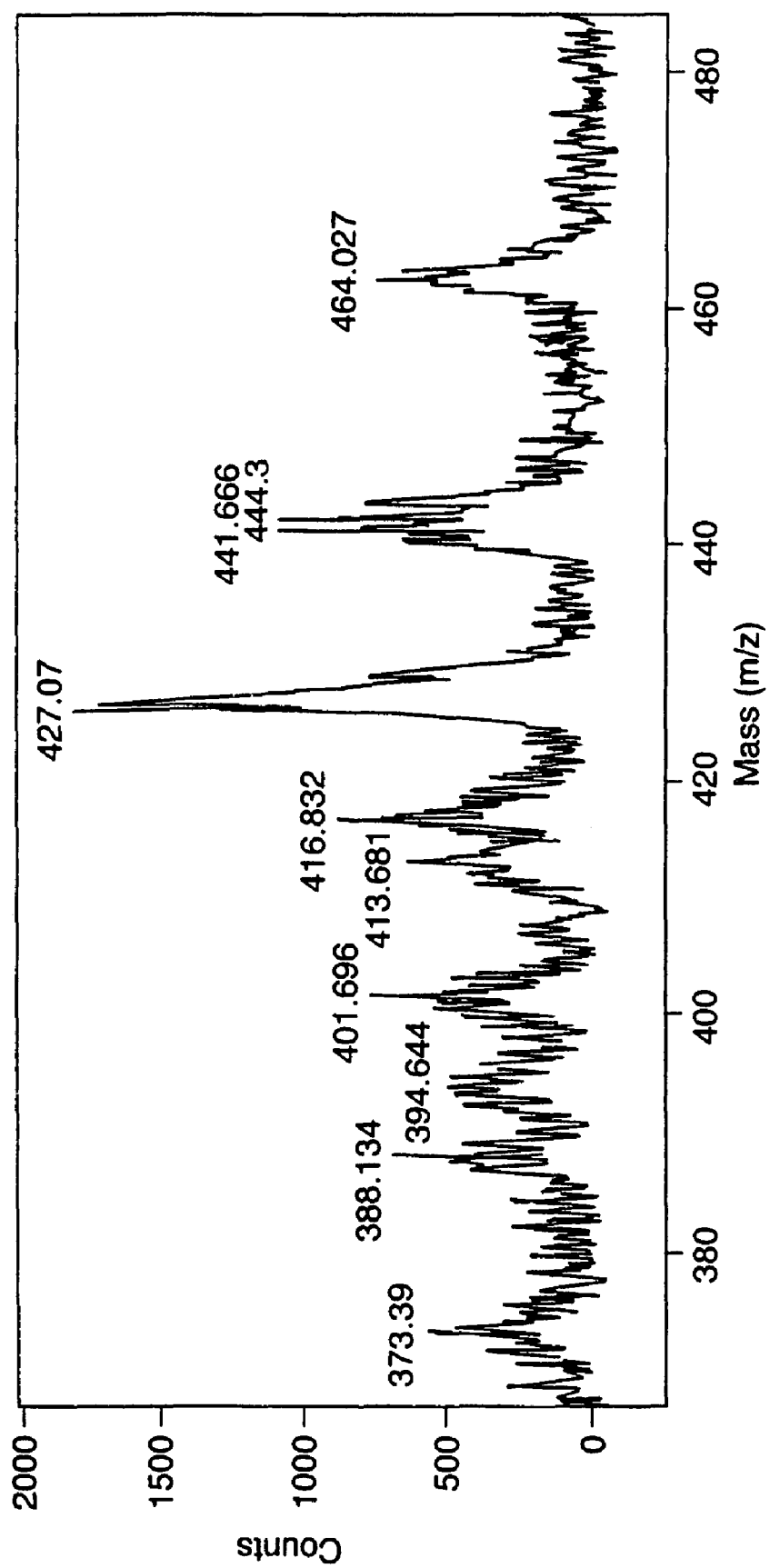
FIGS. 7 and 8 are mass spectra obtained under different conditions as described below.

Derivatised T residues have been coupled with aminated DMT and MMT derivatives as described. A selection of DMT tagged T residues have been mixed together and analysed by mass spectrometry (see FIG. 7.)

Example 4

A disposable glass insert, for use as a target surface for laser desorption ionisation mass spectrometry was manufactured from 1 mm plain soda glass, cut to a rectangle 45 mm×46 mm, and the cut edges bevelled. A standard gold-plated metal insert (Perkin Elmer/Perseptive Biosystems part number VES 503 405) may be used as a template to position orientation markings on the reverse of the glass insert prior to assembly. The insert was held in a disposable sample plate holder (Perkin Elmer/Perseptive Biosystems part number VES 700 314). The 4 retaining screws of the sample holder were removed, the glass insert placed into the upper rectangular frame from behind, and the sample holder was re-assembled. Samples for analysis may be applied using existing methods. Perkin Elmer/Perseptive Biosystems "Voyager"™ Biospectrometry™ Workstation software version 4.03 may be used to correctly locate samples on the plate, and analysis was performed using existing methods.

Figure 8:
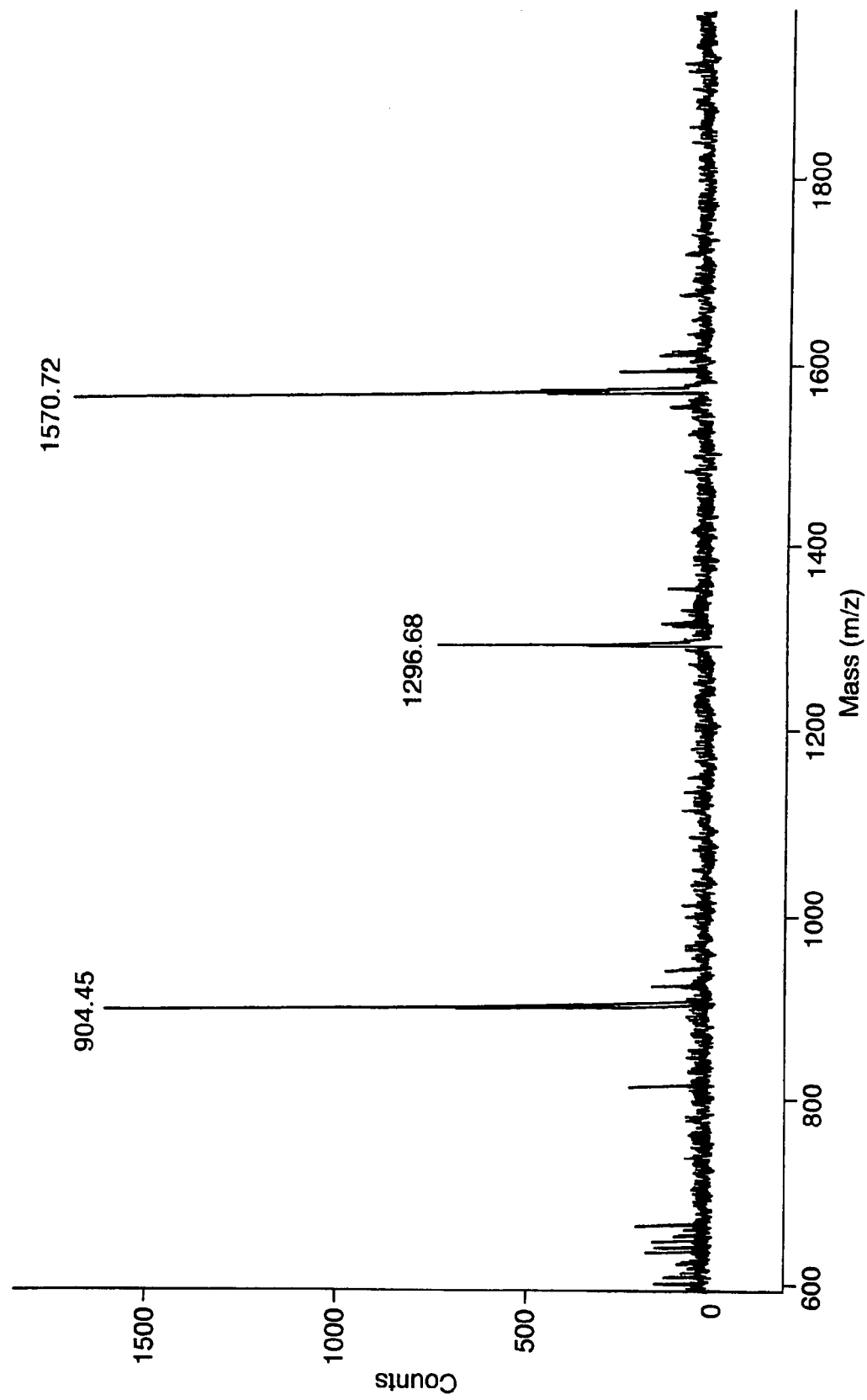

The mass spectrum shown in FIG. 8 was produced by application of the manufacturer's recommended mass calibration mixture to a glass target. The mixture (Perkin Elmer/Perseptive Biosystems part number 2-3243-00-000) comprises 3 peptides des-arg1-bradykinin, angiotensin 1 and glu1-fibrinopeptide B. Analysis was performed using a standard method. The theoretical mass of the singly protonated ion is 904.4681 Da, 1296.6853 Da and 1570.6774 Da respectively Example 5

Polypropylene

In situ synthesis of oligonucleotides directly on to the surface of polypropylene has been described in detail (Matson et al, 1994; Southern et al, 1994). Surface synthesis of a specific short (10-20 bases) sequence can be used to capture a target sequence. Once captured, allele specific oligonucleotides (ASO) can be hybridised to the captured target sequence. Subsequent ligation of a mass tagged oligonucleotide would be used in mass spectrometry to define the allele. Mass spectrometry is enabled by securing the polypropylene array into a disposable sample plat holder in a similar manner to that described in Example 4.

A 9-mer oligonucleotide with DMT left 'on' at the end of conventional phosphoramidite DNA synthesis, was spotted (2000 pmol) on to a piece of polypropylene. Laser Desorption/Ionisation Time of Flight Mass Spectrometry, without matrix revealed a peak at 309.3 mass units. The mass of DMT is 303 mass units. The higher observed mass is due to the polypropylene (strip) target being placed behind the disposable target plate, thereby increasing the ion flight length. The plate was used to keep the polypropylene strip secured for mass spectrometry.

Example 6

Epoxysilane Chemistry

Glass targets are prepared for mass spectrometric analysis as described in Example 4. The surface is activated by treatment with epoxysilane (Beattie et al, 1995) and a target DNA is synthesised with a terminal amine at either the 3' or 5' end. 5 μM of aminated oligonucleotide is spotted on to the surface of the activated glass plate and left from 2 hours to overnight. The surface is washed in $H_2O$ at 60° C., 10 mM triethylamine, pH 9.2, at room temperature, followed by 2 washed in hot water. Hybridisation of a probe oligonucleotide, labelled with a $^{32}P$ radioisotope, is in 3M TMAC, 60 mM Tris pH 7.5, 6 mM EDTA, 0.03% SDS, for 1 hour, followed by a 1 hour wash in the same buffer. Analysis of the hybridisation efficiency can be determined by phosphorimager analysis. Ligation and mass spectrometric analysis of tagged oligonucleotides will determine the allele.

Isothiocyanate Chemistry

This method has been described previously (Weiler and Hoheisel, 1997). For the purpose of these experiments, glass target plates are silanized by immersion in 10% NaOH overnight followed by washing in $H_2O$ and methanol. The plates are then sonicated in 3% aminopropyltrimethoxysilane in methanol, followed by washing in water followed by methanol. The plates are then dried in nitrogen and baked at 110° C. for 15 minutes.

For the immobilisation of aminated oligonucleotides the plates are activated by phenylendiisothiocyanate (PDITC) (Weiler and Hoheisel, 1997). Target oligonucleotides are synthesised with a 5' or 3' amine. Immobilisation of the target DNA is carried out in 0.001 M NaOH, 0.1-1.0 μM oligonucleotide, for 2 hours, at room temperature. Hybridisation of $^{32}P$ radiolabelled complementary probe oligonucleotides is carried out in 3×SSPE and 0.5% SDS for 1 hour followed by washing in the same buffer and subsequent phosphorimager analysis. Ligation and mass spectrometric analysis of tagged oligonucleotides will determine the allele.

Mercaptosilane Modified Glass Surface

This method for the derivitisation of a mercaptosilane modified glass surface has been described previously (Rogers et al, 1999). Briefly, glass target plates are cleaned overnight in 25% ammonium hydroxide, rinsed in water for 10 minutes followed by a brief rinse in anhydrous ethanol. For silanisation, the glass plates are immersed in a 1% solution of 3-mercaptopropyl trimethoxysilane (MPTS), 95% ethanol, 16 mM acetic acid (pH 4.5), for 30 minutes. Finally, the plates are rinsed in 95% ethanol/16 mM acetic acid (pH 4.5) and dried in a vacuum oven for 2 hours at 150° C.

Target DNA is immobilised via a thiol/disulphide exchange reaction. The thiol group can be readily added to the 5' end of any oligonucleotide using standard phosphoramidite chemistry. Typically, 10 μM if thiolated oligonucleotide, in 500 mM $NaHCO_3$ (pH 9.0), is spotted on to the activated mercaptosilane surface, for 2 hours to overnight. The surface is then washed in TNTw buffer (10 mM Tris-HCl, pH 7.5, 150 mM NaCl and 0.05% Tween 20).

A 40 base 5' thiolated oligonucleotide has been immobilised to a mercaptosilanised glass target. Hybridisation of a $^{32}P$ radiolabelled 17 base complementary probe sequence, has demonstrated high specificity for the complementary target sequence with little background hybridisation.

Example 7

Polylysine

A 27-mer oligonucleotide was attached to a glass mass spectrometry target pre-treated with polylysine. After treatment to inhibit non-specific binding, specific hybridisation of a complementary 14-mer with high efficiency has been successfully demonstrated.

A glass MS target (described in Example 4) was cleaned and treated with polylysine solution (Sigma P8920) following the general procedure described below:

1. Place slides in slide racks. Place racks in chambers.

2. Prepare CLEANING SOLUTION: Dissolve 70 g NaOH in 280 ml $ddH_2O$. Add 420 ml 95% ethanol. Total volume is 700 ml (=2×350 ml); stir until completely mixed. If solution remains cloudy, add $ddH_2O$ until clear.

3. Pour solution into chambers with slides; cover chambers with glass lids. Mix on orbital shaker for 2 hrs. Once slides are clean, they should be exposed to air as little as possible. Dust particles will interfere with coating and printing.

4. Quickly transfer racks to fresh chambers filled with ddH$_2$O. Rinse vigorously by plunging racks up and down. Repeat rinses 4× with ddH$_2$O. It is critical to remove all traces of NaOH-ethanol.

5. Prepare POLYLYSINE SOLUTION: 70 ml poly-L-lysine+ 70 ml tissue culture PBS in 560 ml water. Use plastic graduated cylinder and beaker.

6. Transfer slides to polylysine solution and shake for 15 min-1 hr.

7. Transfer rack to fresh chambers filled with ddH$_2$O. Plunge up and down 5× to rinse.

3 oligonucleotides were prepared using standard methods

```
1a
                                         (SEQ ID NO: 7)
5' Cy-GCAGTCAGTC ACAGAAGGTG TTTCTGA 3'

1b
                                         (SEQ ID NO: 7)
5'    GCAGTCAGTC ACAGAAGGTG TTTCTGA 3'

2
                                         (SEQ ID NO: 8)
5' Cy-GAAACACCTT CTGT 3'
```

Oligo 1a is labelled with fluorescent cyanine dye, oligo 1b is the same sequence unlabelled. Oligo 2 is also cyanine labelled and is complementary in sequence to bases 11 to 24 of oligos 1a and 1b.

2-fold serial dilutions of oligos 1a and 1b were prepared in deionised distilled water from 500 ng/µl to 1 ng/µl. Two duplicate 1 µl spots of each dilution were placed on the glass target and allowed to dry in air. The glass target was treated to inhibit non-specific DNA binding following the general procedure described below:

1. Place arrays in slide rack. Have empty slide chamber ready on orbital shaker.

2. Prepare BLOCKING SOLUTION: Dissolve 5.5 g succinic anhydride in 325 ml 1-methyl-2-pyrrolidinone. Immediately after succinic anhydride dissolves, add 25 ml sodium borate.

3. Immediately after sodium borate solution mixes in, pour solution into empty slide chamber. Plunge slide rack in solution several times. Mix on orbital shaker 15-20 min. Meanwhile, heat ~700 ml water (enough to cover slide rack) to 95° C. in 21 beaker.

4. Gently plunge slide rack in 95° C. water for 2 min.

5. Plunge slide rack 5× in 95% ethanol.

Fluorescence was scanned and recorded using a STORM860 fluorescence reader to confirm attachment of oligo 1a. Attachment of the unlabelled oligo 1b of the same sequence is inferred.

Hybridisation solution (4×SSC, 0.25% SDS, 240 pmol oligo 2) was prepared in a total volume of 52 µl, boiled for 2 minutes, placed on to the glass target and covered with an untreated glass target. Hybridisation proceeded for 8 hours in a humid chamber containing 3×SSC at room temperature. The target was then rinsed 3 times in 2×SSC, briefly rinsed in deionised distilled water and allowed to dry in air. Attachment of the labelled oligo 2 to the immobilised, unlabelled complementary sequence oligo 1b was confirmed by fluorescence scanning.

Data

Following treatment to inhibit non specific binding, fluorescence of bound oligo 1a was detected from 500 ng/µl. Post hybridisation, fluorescence of bound oligo 2 was detected across the complete range of dilutions from 500 ng/µl to 1 ng/µl. Non-specific background fluorescence is acceptable.

Example 8

Solution Experiment

A solution experiment was performed to test the ligation of tagged oligonucleotides to template DNA. 9 base oligonucleotides were either tagged or not. A matched oligonucleotide had a mass tag of 413.5 units, and a mismatched oligonucleotide had a mass tag of 402 units. A 17 base primer was used to direct the ligation process. The reaction comprised of combinations of each 9-mer oligonucleotide. The concentrations of template and tagged oligonucleotides was 120 fmol whilst the 17 base primer was at a concentration of 60 fmol. The primer was radiolabelled with $^{32}$P using polynucleotide kinase. Each reaction contained 50 units of *Thermus thermophilus* DNA ligase and was incubated for four hours at either 37° C. or 46° C. The reaction was stopped with formamide and the products analysed by polyacrylamide gel electrophoresis.

The resulting ligated band was excised from the gel and the DNA eluted by incubation in a high salt buffer at 37° C. overnight. The DNA was then purified and analysed by mass spectroscopy without matrix. The resulting mass of 413.5 corresponded to the mass tag used for the ligation of the fully complementary oligonucleotide, N. There was no detectable peak at 402 mass units corresponding to the mismatched sequence of oligonucleotide M. This indicates that the ligation reaction is highly specific for the correctly matched oligonucleotide and is therefore confirmation that the procedures will be adaptable for high throughput genotyping.

Example 9

Abstract

Glass slides were silanised with (3-mercaptopropyl) trimethoxysilane in dry toluene. The terminal thiol function was then reacted with 2,2'-dipyridyl disulfide to form a pyridyl disulfide linkage. A 43-mer oligodeoxynucleotide, modified at its 5'-end with a terminal phosphorothioate group was attached to the modified slides.

Untreated glass slides were soaked in a solution of 5% (v/v) (3-mercaptopropyl)trimethoxysilane in dry toluene for 6 hours. The slides were washed with dry toluene followed by ethanol. The slides were subsequently soaked overnight in a 6.66 g/l solution of 2,2'-dipyridyl disulfide in isopropanol. The slides were finally washed isopropanol and air dried.

The oligonucleotide had the sequence:

5'-p(s)-TTT TAG CAA TGG GCA GTC AGT CAC AGA AGG TGT TTC TGA GAC C 3' (SEQ ID NO: 9)

with p(s)=terminal thiophosphate

Oligonucleotide solutions of 40 µM, 20 µM, 8 µM and 4 µM were prepared in water.

To 20 µl of each dilution, 20 µl 0.8 M Citrate buffer pH 4, 20 µl ethyleneglycol and 40 µl water were added.

Final concentrations were 10 µM, 5 µM, 2 µM and 1 µM.

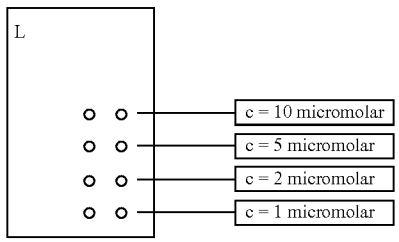

1 μl oligonucleotide solution was applied on each spot. The slides were kept at room temperature for 18 hours, washed with water followed by isopropanol and were allowed to dry.

Example 10

$O^1$-{[4-(succinimidylcarboxy)]-4'-methoxytrityl}-6-trifluoroacetamido-1-hexanol (2). A solution of N-succinimidyl-4-[bis-(phenyl)-chloromethyl]-benzoate (1) (0.8 g, 1.7 mmol) in pyridine (25 ml) at ambient temperature was treated with an excess of 6-trifluoroacetamido-1-hexanol (0.91 g, 4.25 mmol), which was added in small portions as a solid. The resulting solution was stirred overnight at ambient temperature under an atmosphere of nitrogen. The solvent was then removed under vacuum to give a pale yellow oil. Flash column chromatography (5:1 dichloromethane-ethyl acetate) afforded the title compound as a white foam. Yield=0.39 g (35%). δ (300 MHz, $CDCl_3$) 8.02 (2H, d, Aryl), 7.61 (2H, d, Aryl), 7.39-7.20 (9H, m, Aryl), 6.82 (2H, d, Aryl), 6.27 (1H, br, amide), 3.78 (3H, s, $OCH_3$), 3.32 (2H, m), 3.03 (2H, m), 2.87 (4H, s, succinimidyl), 1.62-1.49 (6H, m), 1.42-1.21 (6H, m); IR (film) ν 3345, 1770, 1736, 1708 $cm^{-1}$; MS (ES+) 644 $(M+H_2O)^+$.

$O^1$-{[4-(succinimidylcarboxy)]-4',4"-dimethoxytrityl}-6-trifluoroacetamido-1-hexanol (3) was prepared from N-succinimidyl-4-[(4-methoxydiphenyl)-chloromethyl]-benzoate (4) (1.2 g, 2.5 mmol) and 6-trifluoroacetamido-1-hexanol (1.33 g, 6.25 mmol) using the procedure described above. Yield=1.02 g (62%) as a white foam. $δ_H$ (300 MHz, $CDCl_3$) 8.02 (2H, d, Aryl), 7.61 (2H, d, Aryl), 7.24 (4H, d, Aryl), 6.81 (4H, d, Aryl), 6.26 (1H, br, amide), 3.78 (6H, s, $OCH_3$×2), 3.32 (2H, m), 3.02 (2H, m), 2.86 (4H, s, succinimidyl), 1.6-1.5 (7H, m), 1.36-1.21 (5H, m); IR (film) ν 3400, 1770, 1740, 1708 $cm^{-1}$; MS (ES+) 697 $(M+MeCN)^+$.

$O^1$-{[4-(butylamidocarboxy)]-4'-methoxytrityl}-6-trifluoroacetamido-1-hexanol (5). A solution of $O^1$-{[4-(succinimidylcarboxy)]-4'-methoxytrityl}-6-trifluoroacetamido-1-hexanol (0.39 g, 0.63 mmol) in acetonitrile (5 ml) was treated with an excess of neat n-butylamine (0.18 g, 2.5 mmol, 0.25 ml). The solution was stirred overnight at ambient temperature under an atmosphere of nitrogen. The solvent was then removed under vacuum and the residue partitioned between ethyl acetate and water. The organic layer was separated, dried over $Na_2SO_4$ and filtered. Concentration of the filtrate gave a clear oil which crystallised on standing. Yield=0.35 g (96%). $δ_H$ (300 MHz, $CDCl_3$) 7.64 (2H, d, Aryl), 7.49 (2H, d, Aryl), 7.38 (2H, d, Aryl), 7.27-7.20 (5H, m, Aryl), 6.4 (1H, br, amide), 6.13 (1H, br, amide), 3.77 (3H, s, $OCH_3$), 3.41 (2H, m), 3.29 (2H, m), 3.02 (2H, m), 1.57-1.50 (7H, m), 1.38-1.21 (5H, m), 0.91 (3H, t, $\underline{CH_3}(CH_2)_3N$); IR (film) ν 3303, 3083, 1707, 1637, 1543, 1508 $cm^{-1}$.

$O^1$-{([4-(butylamidocarboxy)]-4',4"-dimethoxytrityl}-6-trifluoroacetamido-1-hexanol (6) was prepared from $O^1$-{[4-(succinimidylcarboxy)]-4',4"-dimethoxytrityl}-6-trifluoroacetamido-1-hexanol (0.5 g, 0.76 mmol) and butylamine (0.22 g, 3.0 mmol, 0.3 ml) using the procedure described above. Yield=0.45 g (95%) as a clear oil. $δ_H$ (300 MHz, $CDCl_3$) 7.64 (2H, m, Aryl), 7.49 (1H, d, Aryl), 7.35 (1H, d, Aryl), 7.34-7.27 (3H, m, Aryl), 7.13 (2H, d, Aryl), 6.79 (4H, m, Aryl), 6.36 (1H, br, amide), 6.05 (1H, br, amide), 3.77 (6H, s, $OCH_3$×2), 3.63 (1H, m), 3.46-3.28 (6H, m), 1.55 (7H, m), 1.37 (4H, m), 0.91 (4H, m); IR (film) ν 3301, 3033, 1708, 1637, 1544, 1508 $cm^{-1}$.

$O^1$-{([4-(butylamidocarboxy)]-4'-methoxytrityl}-6-amino-1-hexanol (7). A solution of $O^1$-{[4-(butylamidocarboxy)]-4'-methoxytrityl}-6-trifluoroacetamido-1-hexanol (0.35 g, 0.6 mmol) in methanol (5 ml) was treated with 0.88spg aqueous ammonia (1 ml) at ambient temperature. The solution was stirred overnight and the solvent then removed under vacuum. Analysis by thin layer chromatography (4:1 dichloromethane-ethyl acetate) showed the presence of a new, polar material which gave positive results when tested for the presence of an amino group (ninhydrin) and trityl residues (anisaldehyde/acid). The crude material was used without further purification.

$O^1$-{([4-(butylamidocarboxy)]-4',4"-dimethoxytrityl}-6-amino-1-hexanol (8) was prepared from $O^1$-{[4-(butylamidocarboxy)]-4',4"-dimethoxytrityl}-6-trifluoroacetamido-1-hexanol (0.45 g, 0.7 mmol) and aqueous ammonia (1 ml) using the procedure described above.

$O^1$-{[4-(butylamidocarboxy)]-4'-methoxytrityl}-6-succinamido-1-hexanol (9). $O^1$-{[4-(butylamidocarboxy)]-4'-methoxytrityl}-6-amino-1-hexanol (~0.3 mmol) was dissolved in anhydrous pyridine (5 ml) at ambient temperature. Succinic anhydride (0.07 g, 0.7 mmol) was then added and the resulting solution stirred at ambient temperature for 2 hours. The solvent was then removed under vacuum and the residue analysed by t.l.c (4:1 dichloromethane-ethyl acetate). A new material was observed ($R_f$ 0.3) which gave a positive result when tested for trityl residues (anisaldehyde/acid), but did not give a positive result when tested for the presence of an amine (ninhydrin). The crude product was used without further purification.

$O^1$-{[4-(butylamidocarboxy)]-4',4"-dimethoxytrityl}-6-succinamido-1-hexanol (10) was prepared from $O^1$-{[4-(butylamidocarboxy)]-4',4"-dimethoxytrityl}-6-amino-1-hexanol (~0.35 mmol) and succinic anhydride (0.09 g, 0.9 mmol) using the procedure described above. The product was used without further purification.

N-succinimidyl {$O^1$-[4-(butylamidocarboxy)]-4'-methoxytrityl}-6-succinamido-1-hexanoate (11). A solution of $O^1$-{[4-(butylamidocarboxy)]-4'-methoxytrityl}-6-succinamido-1-hexanol and O—(N-succinimidyl)-N,N,N',N'-tetramethyluronium tetrafluoroborate in acetonitrile was treated with N,N-(diisopropyl)ethylamine while stirring at ambient temperature. After stirring for 2 hours the solvent was removed under vacuum and the residue subjected to flash column chromatography (98:2 dichloromethane-methanol). A partially purified product was obtained which was then further refined using preparative thin layer chromatography, eluting with 9:1 dichloromethane-methanol. The plate was allowed to dry thoroughly and then eluted again. A band corresponding to a trityl active material on t.l.c was removed, triturated with 9:1 dichloromethane-methanol. The silica was filtered off and the filtrate concentrated under vacuum to give a small amount of the title compound. Yield=10 mg. $δ_H$ (300 MHz, $d_3$-MeCN) 7.68 (2H, d, Aryl), 7.49 (2H, d, Aryl), 7.42

(2H, d, Aryl), 7.33-7.23 (5H, m, Aryl), 7.1 (1H, br, amide), 6.86 (2H, d, Aryl), 6.6 (1H, br, amide), 3.75 (3H, s, OCH$_3$), 3.34-3.27 (2H, m), 3.10 (2H, m), 2.99 (2H, m), 2.56 (4H, s), 2.55-2.38 (4H, m), 1.56-1.49 (3H, m), 1.40-1.29 (7H, m), 1.21 (1H, m), 0.91 (3H, t, C$\underline{H}_3$(CH$_2$)$_3$N).

N-succinimidyl {O$^1$-[4-(butylamidocarboxy)]-4',4''-dimethoxytrityl}-6-succinamido-1-hexanoate (12) was prepared from O$^1$-{[4-(butylamidocarboxy)]-4',4''-dimethoxytrityl}-6-succinamido-1-hexanol (~0.3 mmol), O—(N-succinimidyl)-N,N,N',N'-tetramethyluronium tetrafluoroborate (0.27 g, 0.91 mmol) and N,N-(diisopropyl) ethylamine (0.24 g, 1.9 mmol, 0.33 ml). The product was obtained impure. Yield=0.045 g.

Both of the above compounds were tested for the presence of the active ester by preparing dilute solutions in dichloromethane and then adding an excess of n-butylamine. The reactions were examined by t.l.c (9:1 dichloromethane-methanol) and in both cases showed the complete conversion of the starting material to a more polar product. Reaction of the activated ester with amino nucleotide derivatives could also be expected to result in the formation of similar amide-linked products.

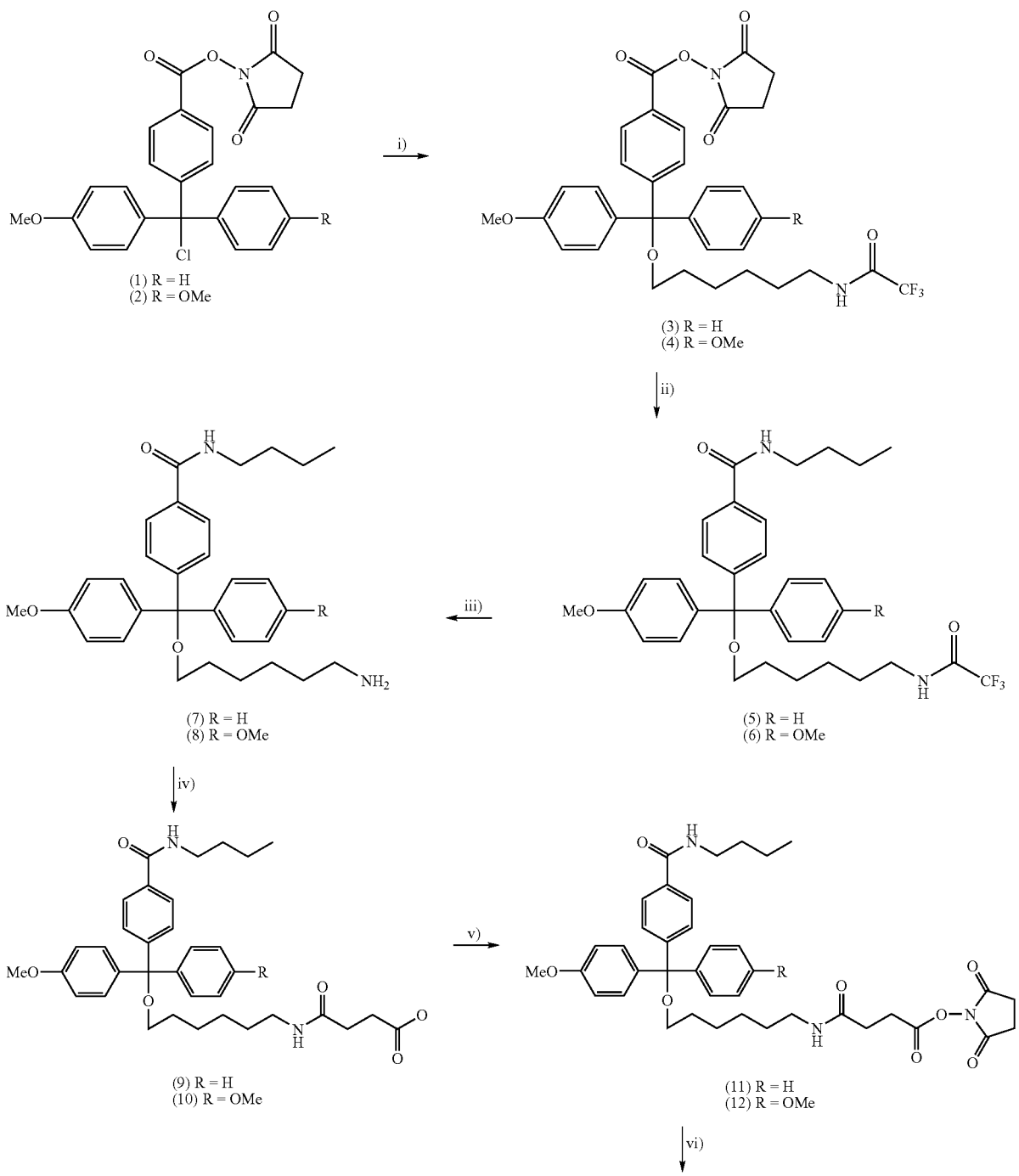

-continued

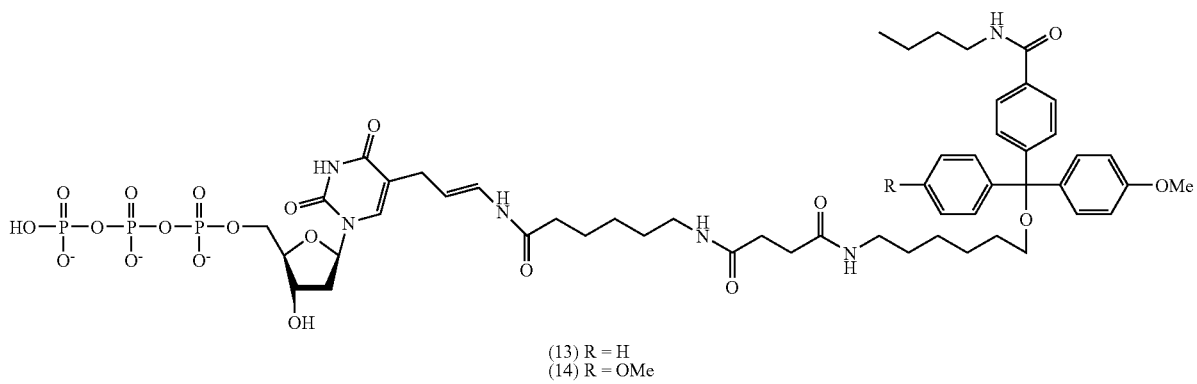

(13) R = H
(14) R = OMe

Reagents; i) HO(CH$_2$)$_6$NHCOCF$_3$, Pyridine, ii) BuNH$_2$, MeCN, iii) NH$_3$, H$_2$O, MeOH, iv) Succinic anhydride, pyridine v) TSTU, DIPEA, MeCN, vi) AACdUTP, 0.2M carbonate buffer, MeCN

Example 11

6-N-Tritylaminosuccinimidylhexanoate

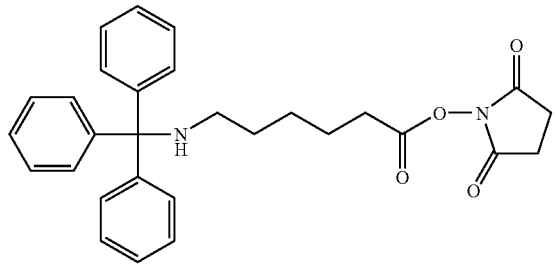

N-Tritylaminocaproic acid (214 mg, 0.57 mmol), dicyclohexylcarbodiimide (154 mg, 0.75 mmol), 4-N-dimethylaminopyridine (21 mg, 0.17 mmol), and N-hydroxysuccinimide (86 mg, 0.75 mmol) were dissolved in dry dioxane (5 ml). The reaction mixture was stirred overnight at room temperature. Dicyclohexylurea was filtered off, and the filtrate was evaporated to dryness and purified by flash chromatography (gradient of dichloromethane to 2% methanol/dichloromethane). Pale yellow foam isolated (270 mg, 98%).

$^1$H NMR (CDCl$_3$, δ, md): 7.46-7.08 (m, 15H, arom), 2.74 (s, 4H, succinimide), 2.53 (t, 2H, NH—C$\underline{H}_2$), 2.06 (t, 2H, COC$\underline{H}_2$), 1.86-1.16 (m, 6H, 3×CH$_2$).

Mass spectrum (Electrospray, +ve mode) 471.53 [M+H]$^+$, 243.28 [Trityl]$^+$.

5-(Allyl-3-biscapromidyl-15-N-tritylamino)-2'-deoxyuridine-5'-triphosphate

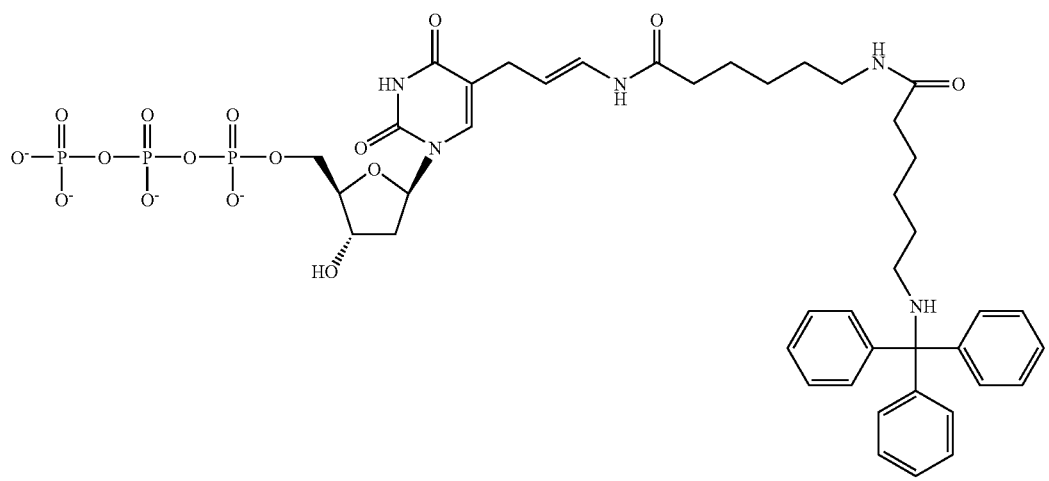

5-(Allyl-3-capromidyl-9-amino)-2'-deoxyuridine-5'-triphosphate (2.5 mg in 500 μl carbonate buffer pH 8.5) was syringed into an Eppendorf with a microstirrer bar. Acetonitrile was added (125 μl), 6-N-tritylaminosuccinimidylhexanoate (6 mg in 45 μl acetonitrile) was then added, followed by addition of more acetonitrile (45 μl). The solution was stirred at room temperature in which the reaction mixture initially went turbid, then clear on further stirring. After 5 hours stirring the reaction mixture was purified on a silica prep. plate with concentrating zone (5:4:1 propan-2-ol: ammonia: water). Silica containing product was scraped from the plate and extracted with the same eluent system, evaporated, redissolved in 50:50 acetonitrile:water and filtered through a cotton wool plug. The solution was evaporated to a fine white powder. TLC after purification indicated the product was higher running than the starting triphosphate and also stained brown on strong heating with anisaldehyde (indicative of sugars).

Mass spectrum (Electrospray, +ve mode) 1014.11[M+Na]$^+$, 243.28 [Trityl]$^+$. (−ve mode) 990.35 [M−H]$^-$, 910.18 [M−H$_2$PO$_3$]$^-$.

Conjugates of allylamino-dUtp such as biotin, haptens, dyes and metal chelates have been reported in the literature as substrates for incorporation by polymerases.

Example 12

Overview

A system of ligating mass-tagged oligo nucleotides to anchored complementary DNA sequences on a solid support via a hybridising third oligo is described. The system uses Tth DNA ligase as an enzymatic component, which catalyses the ligation of a DMT-modified oligo (the "reporter" sequence) onto a hybridising "probe" oligo. The probe oligo, applied in solution, is localised by hybridisation to tethered "template' oligos which remain attached to the solid support throughout all manipulations and detection. Hybridisation of neither the probe nor the reporter oligos will occur at elevated temperatures due to their short length, but the ligated product, with consequent higher Tm, is retained as wash temperatures are raised. The success of the ligation is dependent on the correct mismatch detection of the 3' base on the reporter against the corresponding base on the anchored template. Tth ligase will not catalyse the reaction in the presence of a mismatched base at this position.

Attachment Chemistry

Oligos have been specifically attached to derivatised glass surfaces using a variety of available and developed chemistries. Oligos with a terminal 5' amine group have been used in conjunction with isothiocyanate and epoxide derivatised glass, while thiol-modified oligos have been anchored using mercaptopropyl silane and pyridyl disulphide methods. This latter method, is the subject of the experiments described in this report.

Hybridisation Experiments

The following oligo sequences were used:—

```
                                          (SEQ ID NO:10)
5' TTTTAGCAATGGGCAGTCAGTCACAGAAGGTGTTTCTGAGACC 3'
(template)

(SEQ ID NO:11)
TCAGTCAGTGTCTTCCACAAAGAC* (reporter with mass tag)
(probe)
```

The probe and reporter oligos have Tm values of 42 and 26° C. respectively, allowing both to anneal at the experimental temperature of 22° C. Successive washing at higher temperatures reduces the amount of annealed primer, demonstrated in FIG. 9 for the 15-mer probe, with the greatest reduction occurring in the region of the oligo's Tm. This pattern is consistent for both concentrations of oligo analysed (8 and 6 μM). This indicates that hybridisation is the primary mode of interaction between the probe and template with good signal-to-noise ratios occurring for the higher concentrations of template.

FIG. 10 demonstrates a decrease in signal intensity as template deposition concentrations are lowered. There is considerable variability in the pyridyl disulphide attachment chemistry such that at lower template concentrations hybridization intensity is not consistent.

Demonstration of ligation of both probe and reporter oligos onto the same template and detection by mass spectrometry are continuing.

REFERENCES

Beattie, W G; Meng, L; Turner, S L; Varmer, R S; Dao, D D and Beattie, K L (1995) Hybridization of DNA Targets to Glass-Tethered Oligonucleotide Probes. Molecular Biotechnology, 4, 213-225.

Chen, D; Yan, Z; Cole, D L and Srivatsa, S G (1999) Analysis of internal (n−1) mer deletion sequences in synthetic oligodeoxyribonucleotides by hybridization to an immobilized probe array. Nucleic Acids Res., 27, (2), 3889-995.

Hegner, M., Wagner, P., and Semenza, G. (1993) FEBS 336: 452-456.

Housby, J. N, and Southern, E. M. (1998) *Nucl. Acids. Res.* Submitted.

Matson, R S; Rampal, J B and Coassin, P J (1994) Biopolymer synthesis on polypropylene supports. 1. Oligonucleotides. Anal. Biochem., 220, (1), 225.

Rogers, Y-H; Jiang-Baucom, P; Huang, J.-Z; Bogdanov, V; Anderson, S and Boyce-Jacino, M T (1999) Immobilization of Oligonucleotides onto a Glass Support via Disulphide Bonds: A Method for Preparation of Microarrays. Anal Biochem. 266, 23-30.

Southern, E M; Case-Green, S C; Elder, J K; Johnson, M; Mir, K U; Wang, L and Williams, J C (1994) Arrays of complementary oligonucleotides for analysing the hybridisation behaviour of nucleic acids. Nucleic Acids Res., 22, (8), 1368-1373.

Weiler, J and Hoheisel, J D (1997) Picomole syntheses of high quality oligonucleotide primers in combination with the preparation of oligonucleotide arrays. Nucleosides and Nucleotides, 16, (7-9), 1793-1796.

The invention claimed is:

1. A method, which method comprises providing a labelled oligonucleotide or nucleic acid, and removing the label by cleavage to give a charged species which is subjected to mass spectrometry, wherein the label is a group of formula $R^1R^2R^3C-$, where $R^1$, $R^2$ and $R^3$ are the same or different and each is a monocyclic or fused ring aromatic group that is substituted or unsubstituted.

2. The method of claim 1, wherein nucleic acid sequencing is performed by the use of a labelled primer and/or a labelled hybridisation probe and/or labelled chain extending nucleotides and/or labelled chain terminating nucleotide analogues, wherein the label is one which is removed by cleavage to give a charged species which is subjected to mass spectrometry.

3. An assay method in which a labelled probe is partitioned into two fractions one of which is determined, the probe comprising a ligand joined to a label by a link which is cleavable to give a charged species for mass spectrometry, wherein the label is a group of formula $R^1R^2R^3C-$, where $R^1$, $R^2$ and $R^3$ are the same or different and each is a monocyclic or fused ring aromatic group that is substituted or unsubstituted.

4. The method of claim 3, wherein the ligand is an oligonucleotide.

5. The method of claim 1, wherein at least one of $R^1$, $R^2$ and $R^3$ carries a substituent selected from $C_1$-$C_{20}$ alkoxy or hydrocarbyl either unsubstituted or substituted by carboxylic acid, sulphonic acid, nitro, cyano, hydroxyl, thiol, primary, secondary or tertiary amino, primary or secondary amido, anhydride, carbonyl halide or active ester.

6. The method of claim 1, wherein 4s different labels are used, where the labelled oligonucleotide or nucleic acid contains s bases and each label is indicative of the position and identity of a nucleotide residue of the labelled oligonucleotide or nucleic acid.

7. The method of claim 6, wherein for a base position of the labelled oligonucleotide or nucleic acid, four regions of a mass spectrum corresponding to the masses of the four possible labels (including their isotopic variants) are examined and compared with an expected mass spectrum of the label.

8. The method of claim 1, wherein each possible oligonucleotide or nucleic acid containing s bases is compared in turn against a mass spectrum comprising the s different tag regions, to identify the oligonucleotide having the best fit.

9. The method of claim 1, wherein $R^1R^2R^3C-$ is a substituted monomethoxytrityl group.

10. The method of claim 5, wherein $R^1R^2R^3C-$ is a substituted monomethoxytrityl group.

* * * * *

SEQUENCE LISTING

<160> NUMBER OF SEQ ID NOS: 11

<210> SEQ ID NO 1
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 ttccagt                                                                    7

<210> SEQ ID NO 2
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 ttctatt                                                                    7

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
actggccgtc gttttac                                                        17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aagggcgatc ggtgcgg                                                        17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtaaaacgac ggccagt                                                        17

<210> SEQ ID NO 6
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

-continued

```
cacgacgtt                                                            9

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcagtcagtc acagaaggtg tttctga                                       27

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gaaacacctt ctgt                                                     14

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ttttagcaat gggcagtcag tcacagaagg tgtttctgag acc                     43

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttttagcaat gggcagtcag tcacagaagg tgtttctgag acc                     43

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tcagtcagtg tcttccacaa agac                                          24
```